United States Patent
Johnson et al.

(10) Patent No.: US 9,797,897 B2
(45) Date of Patent: Oct. 24, 2017

(54) ACOUSTICALLY RESPONSIVE PARTICLES

(71) Applicant: DUKE UNIVERSITY, Durham, NC (US)

(72) Inventors: Leah M. Johnson, Durham, NC (US);
Gabriel P. Lopez, Durham, NC (US);
Lu Gao, Chapel Hill, NC (US);
Charles Wyatt Shields, IV, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 291 days.

(21) Appl. No.: 14/388,508

(22) PCT Filed: Mar. 15, 2013

(86) PCT No.: PCT/US2013/032706
§ 371 (c)(1),
(2) Date: Sep. 26, 2014

(87) PCT Pub. No.: WO2013/148376
PCT Pub. Date: Oct. 3, 2013

(65) Prior Publication Data
US 2015/0118692 A1 Apr. 30, 2015

Related U.S. Application Data

(60) Provisional application No. 61/692,011, filed on Aug. 22, 2012, provisional application No. 61/615,524, filed on Mar. 26, 2012.

(51) Int. Cl.
| | |
|---|---|
| *G01N 33/545* | (2006.01) |
| *C08F 30/08* | (2006.01) |
| *C08L 83/04* | (2006.01) |
| *G01N 33/538* | (2006.01) |
| *G01N 33/543* | (2006.01) |
| *G01N 33/58* | (2006.01) |
| *C08G 77/04* | (2006.01) |

(52) U.S. Cl.
CPC .......... *G01N 33/545* (2013.01); *C08F 30/08* (2013.01); *C08L 83/04* (2013.01); *G01N 33/538* (2013.01); *G01N 33/54313* (2013.01); *G01N 33/585* (2013.01); *C08G 77/04* (2013.01)

(58) Field of Classification Search
CPC ......... C08F 30/08; C08G 77/04; C08L 83/04; G01N 33/538; G01N 33/54313; G01N 33/545; G01N 33/585
See application file for complete search history.

(56) References Cited

U.S. PATENT DOCUMENTS

| | | | | |
|---|---|---|---|---|
| 3,872,049 A | * | 3/1975 | Farah ................. | C08G 18/0871 524/590 |
| 8,658,734 B2 | * | 2/2014 | Lopez ................. | A61K 9/0009 524/860 |
| 2012/0065329 A1 | | 3/2012 | Lopez et al. | |

FOREIGN PATENT DOCUMENTS

| | | |
|---|---|---|
| WO | 2010132474 A2 | 11/2010 |
| WO | WO 2010/132471 | * 11/2010 |

OTHER PUBLICATIONS

Laurell T, Petersson F, Nilsson A: Chip integrated strategies for acoustic separation and manipulation of cells and particles. Chem Soc Rev 2007, 36: 492-506.
Lenshof A, Magnusson C, Laurell, T: Acoustofluidics 8: applications of acoustophoresis in continuous flow microsystems. Lab Chip 2012, 12:1210-1223.
Ward M, Turner P, DeJohn M, Kaduchak G: Unit 1.22 Fundamentals of acoustic cytometry. Current Protocols in Cytometry 2009, 49: 122.1-1.22.12.
Piyasena ME, Austin Suthanthiraraj PP, Applegate RW Jr., Goumas AM, Woods TA, López GP, Graves SW: Multinode acoustic focusing for parallel flow cytometry. Anal Chem 2012, 84:1831-1839.
Petersson F, Nilsson A, Holm C, Jönsson H, Laurell T: Separation of lipids from blood utilizing ultrasonic standing waves in microfluidic channels. Analyst 2004, 129:938-943.
Petersson F, Nilsson A, Holm C, Jönsson H, Laurell T: Continuous separation of lipid particles from erythrocytes by means of laminar flow and acoustic standing waves. Lab Chip 2005, 5:20-22.
Petersson F, Aberg L, Sw•rd-Nilsson AM, Laurell T: Free flow acoustophoresis: microfluidic-based mode of particle and cell separation. Anal Chem 2007, 79:5117-5123.
Thévoz P, Adams JD, Shea H, Bruus H, Soh T: Acoustophoretic synchronization of mammalian cells in microchannels. Anal Chem 2010, 82: 3094-3098.
Dykes J, Lenshof A, Astrand-Grundström I, Laurell T, Scheding S: Efficient removal of platelets from peripheral blood progenitor cell products using a novel micro-chip based acoustophoretic platform. PLOS ONE 2011, 6: e23074.
Cushing KW, Piyasena ME, Carroll NJ, Maestas GC, López BA, Edwards BS, Graves SW, López GP: Elastomeric negative acoustic contrast particles for affinity capture assays. Anal Chem, in press, 2013, 85: 2208-2215.
Hu S, Ren X, Bachman M, Sims CE, Li GP, Allbritton N: Surface modification of poly(dimethylsiloxane) microfluidic devices by ultraviolet polymer grafting. Anal Chem 2002, 74: 4117-4123.
Fuard D, Tzvetkova-Chevolleau T, Decossas S, Tracqui P, Schiavone P: Optimization of poly-di-methyl-siloxane (PDMS) substrates for studying cellular adhesion and motility. Microelectron Eng 2008, 85:1289-1293.

(Continued)

*Primary Examiner* — Galina Yakovleva
(74) *Attorney, Agent, or Firm* — NK Patent Law, PLLC

(57) ABSTRACT

Acoustically responsive particles and methods are provided for their use. Methods are provided for making and using tunable, monodisperse acoustically responsive particles and negative contrast acoustic particles, wherein the particles can contain a functional group available for covalent modification.

7 Claims, 26 Drawing Sheets

(56) References Cited

OTHER PUBLICATIONS

Hellmich W, Regtmeier J, Duong TT, Ros R, Anselmetti D, Ros A: Poly(oxyethylene) based surface coatings for poly(dimethylsiloxane) microchannels. Langmuir 2005, 21: 7551-7557.

Efimenko K, Crowe JA, Manias E, Schwark DW, Fischer DA, Genzer, J: Rapid formation of soft hydrophilic silicone elastomer surfaces. Polymer 2005, 46:9329-9341.

Stöber, W. & Fink, A. (1969). Controlled growth of monodisperse silica spheres in the micron size range. Journal of Colloid and Interface Science, 26: 62-69.

Xia, Y., Gates, B., Yin, Y., & Lu, Y. (2000). Monodisperse colloidal spheres: old materials with new applications. Advanced Materials, 12(10): 693-713.

Shields IV, CW; Johnson, LM; Gao, L; López, GP. "Elastomeric Negative Acoustic Contrast Particles for Capture, Acoustophoretic Transport, and Confinement of Cells in Microfluidic Systems," Langmuir 2014. 30(14): 3923-3927.

Johnson, LM; Gao, L; Shields IV, CW; Smith, M; Efimenko, K; Cushing, K; Genzer, J; López, GP. "Elastomeric Microparticles for Acoustic Mediated Bioseparations," Journal of Nanobiotechnology 2013. 11(22): 1-19.

Shields IV, CW; Sun, D; Johnson, K; Duval, K; Rodriguez, AV; Gao, L; Dayton, PA; López, GP. "Nucleation and growth synthesis of functional, monodisperse and acoustically programmable particles," Angewandte Chemie Int'l Edition. 2014. 53(31): 8070-8073.

Ferguson GS, Chaudhury M K, Biebuyck H, Whitesides GM: Monolayers on disordered substrates: self-Assembly of alkyltrichlorosilanes on surface-modified polyethylene and poly(dimethylsiloxane). Macromol 1993, 26: 5870-5875.

Linder V, Verpoorte E. Thorman W. de Rooij NF, Sigrist H: Surface biopassivation of replicated poly(dimethylsiloxane) nicrofluidic channels and application to heterogeneous immunoreaction with on-ship fluorescence detection. Anal Chem 2001, 73: 4181-4189.

\* cited by examiner

FIG.'s 19A-19D

ACOUSTICALLY RESPONSIVE PARTICLES

CROSS REFERENCE TO RELATED APPLICATIONS

This application is a CFR section 371 national phase application of International Patent Application No. PCT/US2013/032706 filed on Mar. 15, 2013, which claims the benefit of U.S. Provisional Patent Application No. 61/615,524, filed Mar. 26, 2012 and titled ELASTOMERIC PARTICLES FOR BIO-ANALYSIS AND METHODS OF USE, and U.S. Provisional Patent Application No. 61/692,011, filed Aug. 22, 2012 and titled FUNCTIONALIZED MONODISPERSE ACOUSTICALLY RESPONSIVE COLLOIDS FROM NUCLEATION AND GROWTH, the disclosures of which are incorporated herein by reference in their entireties.

STATEMENT OF GOVERNMENT SUPPORT

This invention was made with U.S. Government support under the National Science Foundation grant no. CBET-1050176 and DMR-1121107. The U.S. Government has certain rights in the invention.

TECHNICAL FIELD

The present disclosure relates to acoustically responsive particles. Particularly, the present disclosure relates to methods for making and using tunable, monodisperse acoustically responsive particles and negative contrast acoustic particles, wherein the particles can contain a functional group available for covalent modification.

BACKGROUND

Particles respond to an applied acoustic standing wave by transporting to specific locations along the wave (i.e., pressure node, pressure antinode). This relocation is dictated by the contrast factor (i.e. positive contrast, negative contrast) which originates from differences in density and elasticity between the particle and the surrounding media. For example, particles with positive contrast (e.g., incompressible polystyrene beads, cells) in aqueous media are generally transported to acoustic pressure nodes. On the other hand, compressible, silicone elastomeric particles (NACPs) have a negative contrast property that is opposite to commonly used particles (e.g., polystyrene beads)[1-2]. Consequently, NACPs move to acoustic pressure anti-nodes when subjected to acoustic standing waves, which is a direction opposite from common, incompressible particles.

The capacity to relocate incompressible particles such as cells to pressure nodes has been used in various approaches for focusing and separation of mammalian cells.[3-9] For example, the recently commercialized ATTUNE flow cytometer (LIFE TECHNOLOGIES) substitutes traditional hydrodynamic focusing with ultrasonic standing wave fields to focus cells into a single flowing stream prior to laser interrogation.[3] To increase the high-throughput capacity of flow cytometry, Piyasena et al. recently developed multi-node acoustic focusing and demonstrated up to 37 parallel flow streams.[4] Peterson et al. exploited the inherent contrast factor of constituents from whole blood to separate and sort positive contrast erythrocytes from negative contrast lipids within an acoustofluidic device.[5,6]

One current drawback of using negative acoustic contrast elastomeric particles to relocate incompressible particles such as cells to pressure nodes is that the elastomeric particles are not amenable to covalent modification with a specifically desired molecular recognition molecule. For example, PCT Patent Application Publication WO 2010/132474A2 discloses 'Stable Elastomeric Negative Acoustic Contrast Particles and Their Use in Acoustic Radiation Fields', but does not teach preparation of stable, elastomeric particles using starting materials with functional groups available for covalent modification with biological moieties. For instance, WO 2010/132474A2 only describes the use of inert silicone starting material (i.e., polydimethyl siloxane (PDMS)) without available groups for biofunctionalization in which to synthesize the elastomeric particles. Recently, Cushing et al. reported using protein adsorption as a way of modifying the surface of such negative acoustic contrast PDMS particles for biomolecule quantification assays.[10] While protein adsorption may be convenient, such adsorption techniques often generate heterogeneous surfaces resulting from random orientation and denaturation of proteins on the surface.[11] These considerations become more important in cell sorting applications that require high concentrations of active, surface-presenting bioaffinity groups for capturing rare cells and cells with a low quantity of targeted surface antigens.

In addition to the use of negative acoustic contrast elastomeric particles for bioseparations in acoustofluidic devices, negative and positive acoustic contrast particles have utility in many industrial fields such as those fields involving the production of paints, foods, inks, coatings, films, cosmetics, and rheological fluids. Using bulk synthetic approaches to synthesize monodisperse colloids with useful biochemical and mechanical properties represents a longstanding goal in synthetic chemistry, chemical engineering, bioengineering, and mechanical engineering. Rapid and scalable synthesis of vast quantities of monodisperse colloids appeals to many industrial fields involving the production of paints, foods, inks, coatings, films, cosmetics, and rheological fluids.[20] Monodisperse colloids also garner significant importance in scientific communities with examples in the production of slurries, clays, minerals, aerosols, foams, macromolecules, sols, semiconductor nanocryistallites, silica colloids, and biochemical interfaces with proteins, viruses, bacteria, and cells.[20]

As described above, utilization of acoustic contrast colloids in biological applications, such as diagnostic screenings or immunological bio-marker assays, would require the presence of ample functional groups for various binding and bio-conjugation reactions. The ability to rapidly synthesize functional, monodisperse colloids with controlled mechanical properties (i.e., specific bulk modulus and density) is desirable as it would allow for tight responsive control in acoustic fields. Particles designed with high bulk moduli and densities exhibit positive acoustic contrast coefficients, indicating transport to the acoustic pressure nodes of standing waves.[5] Conversely, particles designed with low bulk moduli and densities exhibit negative acoustic contrast coefficients, indicating transport to the acoustic pressure anti-nodes of standing waves.[5] Predicate models for colloid synthesis have failed to fabricate tightly monodisperse colloids with a tunable acoustic response (i.e., exhibiting either positive or negative acoustic contrast by altering the mechanism of synthesis) via bulk synthetic methods.

Accordingly, there remains an unmet need for acoustic contrast particles with functional groups that would allow for a range of binding and bio-conjugation reactions. In addition, there remains an unmet need for monodisperse acoustic contrast colloids that can be produced via bulk synthetic methods, and also for such monodisperse particles that can be produced with covalently modifiable functional groups that can be produced via bulk synthetic methods. The presently disclosed subject matter provides such particles.

SUMMARY

Certain aspects of the presently disclosed subject matter having been stated hereinabove, which are addressed in whole or in part by the presently disclosed subject matter, other aspects will become evident as the description proceeds when taken in connection with the accompanying Examples and Figures as best described herein below.

In accordance with an aspect provided herein, a method for synthesizing elastomeric negative contrast acoustic particles having a functional group available for covalent modification is provided. The method includes emulsifying an elastomer pre-polymer including a functional group with a catalyst in the presence of a surfactant under conditions sufficient to produce emulsion droplets, and curing the emulsion droplets under conditions sufficient to form stable elastomeric negative acoustic contrast particles that have a functional group available for covalent modification.

In accordance with an aspect provided herein, the method includes covalently modifying the available functional group with a moiety for binding to a target of interest.

In accordance with an aspect provided herein, the target of interest includes one of a cell, a protein, a receptor, an antibody, an antigen, a drug, virus, nucleic acid, a polysaccharide or a metabolite.

In accordance with an aspect provided herein, a method for acoustic-mediated bioanalysis is provided. The method includes exposing a fluid sample suspected of containing a target of interest to a plurality of elastomeric negative contrast acoustic particles disclosed herein. The functional group of the particles includes a covalently attached moiety for binding to the target of interest, under conditions sufficient that the moiety binds to the target. The method includes subjecting the fluid sample to acoustic radiation pressure from an acoustic standing wave sufficient within an acoustic focusing chamber to focus the particles to the acoustic pressure antinodes such that the target is separated from other components in the sample.

In accordance with an aspect provided herein, the method includes removing any positive acoustic contrast particles from the acoustic focusing chamber.

In accordance with an aspect provided herein, the method includes removing the negative contrast acoustic particles from the acoustic focusing chamber and analyzing the particles.

In accordance with an aspect provided herein, a method for synthesizing elastomeric negative contrast acoustic particles having a covalently functionalized surfactant for recognition of a target of interest is provided. The method includes emulsifying an elastomer pre-polymer with a catalyst in the presence of a surfactant under conditions sufficient to produce emulsion droplets, wherein the surfactant is covalently functionalized to allow for binding to a target of interest and curing the emulsion droplets under conditions sufficient to form stable elastomeric negative acoustic contrast particles having the functionalized surfactant available for binding to the target of interest.

In accordance with an aspect provided herein, the target of interest includes one of a cell, a protein, a receptor, an antibody, an antigen, a drug, polysaccharide, or a metabolite.

In accordance with an aspect provided herein, the elastomeric negative contrast acoustic particle is functionalized such that binds to the target of interest.

In accordance with an aspect provided herein, an elastomeric negative contrast acoustic particle made according to any of the methods provided herein is disclosed.

In accordance with an aspect provided herein, a method for acoustic-mediated bioanalysis is provided. The method includes exposing a fluid sample suspected of containing a target of interest to a plurality of elastomeric negative contrast acoustic particles under conditions sufficient that the functionalized surfactant binds to the target of interest, and subjecting the fluid sample to acoustic radiation pressure from an acoustic standing wave sufficient within an acoustic focusing chamber to focus the particles to the acoustic pressure antinodes such that the target is separated from other components in the sample.

In accordance with an aspect provided herein, a method for bulk synthesis of monodisperse, tunable contrast acoustic particles is provided. The method includes agitating varying ratios of one of a di-functional, a tri-functional, and a tetra-functional siloxane monomer in an aqueous solution such that hydrolysis and uniform condensation occur upon addition of a catalyst and monodisperse acoustic contrast particles are formed. The tunable acoustic contrast of the monodisperse particles formed is based on the ratios of the di-functional, tri-functional, and tetra-functional siloxane monomers used.

In accordance with an aspect provided herein, the siloxane monomer includes a conjugative group such that the group is available for covalent modification in the formed monodisperse particles.

In accordance with an aspect provided herein, a monodisperse, acoustic contrast particle made according to one or more methods disclosed herein is provided.

In accordance with an aspect provided herein, a monodisperse, acoustic contrast particle has a conjugative group that is covalently modified with a moiety for binding to a target of interest.

In accordance with an aspect provided herein, the target of interest of the particle includes one of a cell, a protein, a receptor, an antibody, a virus, an antigen, a drug, and a metabolite.

In accordance with an aspect provided herein, a method for bulk synthesis of monodisperse, tunable contrast acoustic particles is provided. The method includes agitating in an acidic aqueous solution varying ratios of one of a di-functional, a tri-functional, and a tetra-functional siloxane monomer under conditions sufficient to allow for hydrolysis and the formation of oligomers, and adding a catalyst and continuing to agitate the solution under alkaline pH conditions sufficient to allow for a condensation reaction and formation of monodisperse acoustic contrast particles. The tunable acoustic contrast of the monodisperse particles formed is based on the ratios of the di-functional, tri-functional, and tetra-functional siloxane monomers used.

In accordance with an aspect provided herein, the siloxane monomer includes a conjugative group such that the group is available for covalent modification in the formed monodisperse particles.

In accordance with an aspect provided herein, a monodisperse, acoustic contrast particle made according to the one or more methods disclosed herein is provided.

In accordance with an aspect provided herein, the conjugative group is covalently modified with a moiety for binding to a target of interest.

In accordance with an aspect provided herein, the target of interest includes one of a cell, a protein, a virus, a receptor, an antibody, an antigen, a drug, and a metabolite.

In accordance with an aspect provided herein, a method for synthesizing monodisperse, tunable contrast acoustic particles is provided. The method includes agitating in an acidic aqueous solution varying ratios of one of a di-functional, a tri-functional, and a tetra-functional siloxane monomer under conditions sufficient to allow for hydrolysis and the formation of oligomers. The method may include removing a majority of the large non-uniform oligomers from the smaller hydrolyzed oligomers and adding a catalyst and continuing to agitate the solution under conditions sufficient to allow for a uniform condensation reaction and formation of monodisperse acoustic contrast particles. The tunable acoustic contrast of the monodisperse particles formed is based on the ratios of the di-functional, tri-functional, and tetra-functional siloxane monomers used.

In accordance with an aspect provided herein, the siloxane monomer includes a conjugative group such that the group is available for covalent modification in the formed monodisperse particles.

In accordance with an aspect provided herein, the conjugative group is covalently modified with a moiety for binding to a target of interest.

In accordance with an aspect provided herein, the target of interest includes one of a cell, a protein, a receptor, a virus, an antibody, an antigen, a drug, a polysaccharide or a metabolite.

In accordance with an aspect provided herein, a method for synthesizing monodisperse, tunable contrast acoustic particles is provided. The method includes agitating in an acidic aqueous solution varying ratios of one of a tri-functional and a tetra-functional siloxane monomer under conditions sufficient to allow for hydrolysis and the formation of oligomers, agitating in a separate acidic aqueous solution one or more of a di-functional siloxane monomer and under conditions sufficient to allow for hydrolysis and the formation of oligomers, removing from the di-functional solution a majority of the large non-uniform oligomers from the smaller hydrolyzed oligomers, adding a catalyst for uniform condensation, and continuing to agitate the solution, and removing from the tri- and tetra-functional solution a majority of the large non-uniform oligomers from the smaller hydrolyzed oligomers, adding the tri- and tetra-functional solution directly to the di-functional solution, adding a catalyst and continuing to agitate the solution under conditions sufficient to allow for a condensation reaction and formation of monodisperse acoustic contrast particles. The tunable acoustic contrast of the monodisperse particles formed is based on the ratios of the di-functional, tri-functional, and tetra-functional siloxane monomers used.

In accordance with an aspect provided herein, the siloxane monomer includes a conjugative group such that the group is available for covalent modification in the formed monodisperse particles.

In accordance with an aspect provided herein, the conjugative group is covalently modified with a moiety for binding to a target of interest.

In accordance with an aspect provided herein, the target of interest includes one of a cell, a protein, a receptor, a virus, an antibody, an antigen, a drug, a polysaccharide or a metabolite.

BRIEF DESCRIPTION OF THE DRAWINGS

The foregoing summary, as well as the following detailed description of various embodiments, is better understood when read in conjunction with the appended figures. For the purposes of illustration, there is shown in the Figures exemplary embodiments; however, the presently disclosed subject matter is not limited to the specific methods and exemplary embodiments disclosed.

DETAILED DESCRIPTION

Figure 1A:
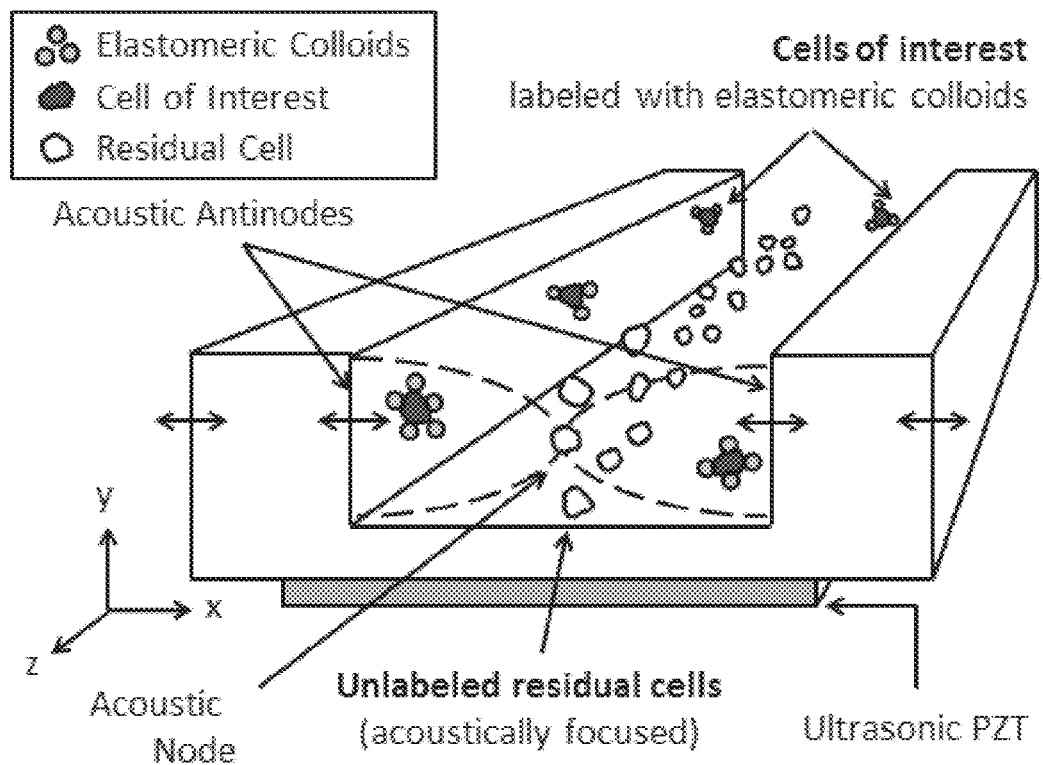
FIGS. 1A-1B are schematic drawings showing a system for acoustic cell sorting using either the negative acoustic contrast particles (NACPs) or FMAR (functional monodisperse and acoustically responsive) negative contrast colloids according to one or more embodiments of the present disclosure. A) Rapid and continuous cell sorting in acoustic field. Unlabeled "residual" cells focus in the acoustic node within the microfluidic channel via forces from an acoustic standing wave. Cells captured by the negative contrast particles of the present disclosure displace to the acoustic antinodes whereas unbound cells focus in the acoustic node. B) Channel Cross Section. Note: components are not to scale and the glass lid of the acoustofluidic device is not shown.

The presently disclosed subject matter now will be described more fully hereinafter with reference to the accompanying Figures, in which some, but not all embodiments of the presently disclosed subject matter are shown. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Figures. Therefore, it is to be understood that the presently disclosed subject matter is not to be limited to the specific embodiments disclosed and that modifications and other embodiments are intended to be included within the scope of the appended claims.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

The terms "particles" and "colloids" are herein used interchangeably for the purposes of the specification and claims.

Unless otherwise defined, all technical terms used herein have the same meaning as commonly understood by one of ordinary skill in the art to which this disclosure belongs.

In one aspect, the present disclosure provides negative and positive acoustic contrast particles (NACPs) and (PACPs), respectively, that allow for covalent modification of the particles such that the particles can be modified with specific biomolecular recognition molecules. In another aspect, the present disclosure provides methods for bulk synthesis of monodisperse, tunable contrast acoustic particles, where the tunable acoustic contrast of the monodisperse particles formed is based on the ratios of the di-functional, tri-functional, and tetra-functional siloxane monomers used. The monodisperse, tunable acoustic contrast particles are synthesized using a nucleation and growth method and these particles can also be functionalized to allow for specific covalent modification. Thus, the monodisperse and acoustically responsive particles synthesized using a nucleation and growth method may be referred to herein as monodisperse and acoustically responsive (FMARs). The acoustic contrast particles of the present disclosure will now be described in further detail.

An important goal is to be able to employ negative acoustic contrast particles (NACPs) for bioanalytical techniques that require biofunctionalization of the particle surface for binding to specific biomolecules or cells. Common bioconjugation schemes, such as carboiimide chemical approaches, are not feasible with NACPs synthesized using the common silicone material (e.g., PDMS), because the resulting PDMS NACPs lack the necessary functional groups such as carboxylates, hydroxyls, epoxies, and amines to introduce functionality. To address this problem, in one example, PVMS pre-polymers were used to generate NACPs with surface vinyl groups that would be useful for reactions such thiolene. In this manner, a variety of chemical reactions can be employed to functionalize the vinyl containing NACPs. In another example, NACPs were synthesized in the presence of a covalently functionalized surfactant to allow for binding to a target of interest.

Figure 1B:
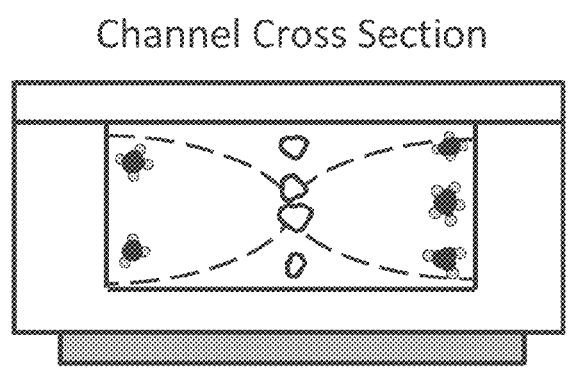

Thus, in one aspect, the particles of the present disclosure augment existing acoustophoretic particle sorting capabilities and relocation of PACPs to antinodes of ultrasound standing waves. FIG. 1 illustrates the principle. Central to this bioseparation scheme is the specific association between the engineered NACPs and targeted PACPs to create a stable complex capable of in-tandem transport to the acoustic antinode. This requires precise design of biofunctional NACPs that exhibit stability and specificity for targeted PACPs. Thus, in one aspect, the present disclosure provides the design, preparation, and application of NACPs for bioanalytical techniques.

The design, preparation, and utilization of biospecific NACPs hold great potential for a platform technology. NACPs are applicable to a large number of biomedical analytical applications (e.g. rare cell and marker isolation, detection and analysis) as well as therapeutic applications (continuous separation applications for removing cellular and large molecular analytes from complex samples such as blood). Similar to the universality of magnetic particles, acoustic-responsive NACPs may also be employed in a variety of applications, but with the added benefit that nonelastic particles (i.e., components not bound to NACPs) are also affected by the applied acoustic field, thus enabling highly sensitive and continuous separations. In one non-limiting example, NACPs can be employed, in conjunction with acoustic microfluidic cells, to enrich rare cells from complex cellular admixtures.

In the present disclosure, silicone NACPs were prepared that contained stable, covalently bound biofunctional groups on the NACP surface. Silicone was chosen for the particle material due to its high compressibility that enables use in acoustic-based bioanalysis. However, silicone material is notoriously difficult to functionalize owing to the inertness of the material. Moreover, silicone particles often irreversibly aggregate, thereby making use in bioassays quite difficult. The ability to create stable, disperse NACPs that contain reactive, surface-presenting biological moieties is the key to enabling acoustic-mediated bioseparation and bioassays. NACPs require stability during downstream manipulation steps (e.g., washing steps) without aggregation or loss of bio-activity. The present disclosure enables said requirements by teaching 1) NACP preparation from silicone starting materials that contain functional groups (e.g., vinyl groups) to permit immediate, covalent bioconjugation of NACP surfaces; and 2) NACP preparation conditions that avoid particle aggregation. In one example, polyvinylmethyl siloxane (PVMS) was employed as a starting material that undergoes alkoxy condensation curing reactions to ultimately generate NACPs with surface-based vinyl groups.

The preparation of stable, bio-functional NACPs is key to permitting acoustic-based bioassays and bioseparation. The choice of surfactant employed during NACP homogenization preparation markedly affected NACP stability during downstream manipulation steps involving centrifugation and biofunctionalization. For example, surfactants such as cetyl trimethylammonium bromide (CTAB) and Tween-20 resulted in irreversible aggregation during attempts to resuspend NACPs with physiological buffers (PBS, pH=7.3) post-centrifugation. Alternatively, nonionic triblock copolymer surfactants with hydrophile-lipophile (HLB) values >24 (e.g., PLURONIC F108, FIOS, PLURONIC F68) permitted preparation of stable NACPs capable of withstanding numerous centrifugation wash cycles without aggregation. The use of these surfactants to maintain stable, non-aggregated NACPs in physiological buffers is a critical finding that enables use of these NACPs in biological applications.

The results presented herein demonstrate the ability of negative acoustic contrast particles (NACPs) to specifically capture and transport positive acoustic contrast particles (PACPs) to the antinode of an ultrasound standing wave. Emulsification and post curing of pre-polymers, either polydimethylsiloxane (PDMS) or polyvinylmethylsiloxane (PVMS), within aqueous surfactant solution resulted in the formation of stable NACPs that can focus onto acoustic antinodes. Both photochemical reactions with biotin-tetrafluorophenyl azide (biotin-TFPA) and end-functionalization of PLURONIC F108 surfactant to biofunctionalize NACPs was demonstrated. These biotinylated NACPs can bind specifically to streptavidin polystyrene microparticles (as cell surrogates) and transport them to the acoustic antinode within an acoustofluidic chip as shown in the results and figures provided herein.

In another aspect, the present disclosure provides methods for bulk synthesis of monodisperse, tunable contrast acoustic particles, where the tunable acoustic contrast of the monodisperse particles formed is based on the ratios of the di-functional, tri-functional, and tetra-functional siloxane monomers used. Predicate models for colloid synthesis have failed to fabricate tightly monodisperse colloids with a tunable acoustic response (i.e., exhibiting either positive or negative acoustic contrast by altering the mechanism of synthesis) via bulk synthetic methods. The method provided in the present disclosure "nucleation and growth" solves this problem by synthesis of particles in a two-step process that includes 1) uniform hydrolysis of monomeric siloxane species to form monodisperse nuclei, and 2) uniform growth of colloids by polycondensation of monomers in solution.

Further, known methods for synthesis of monodisperse colloids from bulk synthesis generally result in inert silicones, which cannot be readily bio-functionalized to covalently interact with surrounding entities. In the present disclosure, siloxane monomers bearing at least one functional group are incorporated during the synthesis process such that the entire microparticle bares ample reactive sites for various conjugations. The FMAR colloids of the present disclosure represent a unique class of particles that exhibit three distinct and useful characteristics.

(1) FMAR colloids provide ample reactive groups on the colloidal surface (or within the colloid) for various reactions with biological moieties (e.g., bio-conjugations) or with synthetic compounds.

(2) The FMAR colloids of the present disclosure can meet specific size requirements as possessing average diameters within a predefined threshold of variance. Precise definitions of monodispersity range, though the National Institute of Standards and Technology (NIST) defines monodispersity as a population of particles possessing a radial coefficient of variance of 5% or less. The bulk synthetic approaches of the present disclosure provide a tight limit to the overall size dispersity, and the colloids synthesized according to these methods have a monodispersity defined as having a radial coefficient of variance of 15% or less.

(3) The FMAR colloids of the present disclosure possess specific bulk moduli (i.e., compressibility) and densities such as to be considered acoustically responsive. Acoustically responsive is defined herein as spatially displacing either to the node or the antinode of an acoustic pressure standing wave. The FMAR colloids presented herein can be designed to exhibit either positive or negative acoustic contrast, allowing the particles to spontaneously align in the acoustic node and antinode of a standing wave, respectively. The type of acoustic response in the colloid can be controlled by varying the degree of crosslinking density. For example, incorporating large ratios of tri- and tetra-functional monomeric species (monomers containing three or four siloxane bonds) into the synthesis of FMAR colloids leads to a high crosslinking density and particles exhibit more rigid characteristics, yielding a positive acoustic contrast factor. Conversely, incorporating large ratios of di- and tri-functional monomeric species into the synthesis of FMAR can lead to a low crosslinking density and particles exhibit compressible characteristics, yielding a negative acoustic contrast factor.

The FMAR colloids of the present disclosure exhibit several key qualities that enable their use in a variety of applications. The functional groups on the microparticles allow for the stable covalent conjugation of synthetic materials and biomolecules on or within the FMAR colloids. Notwithstanding, various functional and non-functional surfactants can be used to coat the particles to increase stability and prevent aggregation for a variety of additional uses. The FMAR colloids of the present disclosure harness the potential for application in a myriad of industrial pursuits due to the ability to use a bulk synthesis production method for production of the monodisperse microparticles. These industries include, but are not limited to paints, foods, inks, coatings, films, cosmetics, rheological fluids, slurries, clays, minerals, aerosols, foams, macromolecules, sols, semiconductor nanocrylstallites, silica colloids, and biochemical interfaces.

The functionalized monodisperse acoustically responsive (FMAR) colloids of the present disclosure describe a range of microparticle characteristics in one uniform colloidal suspension. The FMAR colloids can be easily synthesized to possess ample functional groups throughout the polymer construct for facile bio-conjugations and synthetic reactions in biosensing, screening, separation, marking, coating, and signaling applications. FMAR colloids can be synthesized in bulk to exhibit size monodispersity within a predefined threshold, allowing for direct incorporation to industrial products including, but not limited to, paints, foods, cosmetics, aerosols, coatings, and films. The synthesis procedure for FMAR colloids can allow for the ability to control the mechanical properties of colloids such that either positive acoustic contrast or negative acoustic contrast characteristics are attained, depending on the application of interest.

The functionalized monodisperse acoustically responsive (FMAR) colloids of the present disclosure can to bind to specific analytes (i.e., rigid moieties such as molecules, rigid polystyrene beads, or cells) and relocate those captured analytes from the acoustic pressure node to the antinode for collection as shown in the results and figures provided herein.

In accordance with an aspect provided herein, a method for synthesizing elastomeric negative contrast acoustic particles having a functional group available for covalent modification is provided. The method includes emulsifying an elastomer pre-polymer including a functional group with a catalyst in the presence of a surfactant under conditions sufficient to produce emulsion droplets, and curing the emulsion droplets under conditions sufficient to form stable elastomeric negative acoustic contrast particles that have a functional group available for covalent modification.

In accordance with an aspect provided herein, the elastomer pre-polymer includes a silicone material.

In accordance with an aspect provided herein, the functional group includes one of vinyl, carboxylate, hydroxyl, epoxide, sulfhydryl, amide, acrylate, thiol, azide, maleimide, isocyanate, aziridine, carbonate, N-hydroxysuccinimide ester, imidoester, carbodiimide, anhydride, succinimidyl carbonate, and amine, and combinations thereof.

In accordance with an aspect provided herein, the elastomer pre-polymer includes polyvinylmethylsiloxane (PVMS).

In accordance with an aspect provided herein, the surfactant is a nonionic surfactant including one of PLURONIC F108, PLURONIC F68, PLURONIC P103. PLURONIC F98. PLURONIC P84, PLURONIC F127, PLURONIC F88, PLURONIC F77, PLURONIC P84, and FIOS, or an ionic surfactant including one of CHAPS, betaines, lecithin, phosphates, cetyl trimethylammonium bromide (CTAB), hexadecyl trimethyl ammonium bromide, cetyl trimethylammonium chloride (CTAC), cetylpyridinium chloride (CPC), benzalkonium chloride (BAC), Benzethonium chloride (BZT), ammonium lauryl sulfate, and sodium lauryl sulfate, and combinations thereof.

In accordance with an aspect provided herein, the nonionic surfactant includes a PLURONIC surfactant having greater than 50 end groups of polyethylene oxide (PEO).

In accordance with an aspect provided herein, the nonionic surfactant includes a triblock copolymer surfactant having a hydrophile-lipophile (HLB) value greater than 24.

In accordance with an aspect provided herein, the method includes covalently modifying the available functional group via a thiolene reaction, a thermal-initiated reaction, or a photo-initiated reaction.

In accordance with an aspect provided herein, the method includes covalently modifying the available functional group with a moiety for binding to a target of interest.

In accordance with an aspect provided herein, the moiety includes a biotin or a streptavidin for binding to the target of interest that includes a binding partner for the biotin or the streptavidin.

In accordance with an aspect provided herein, the target of interest includes one of a cell, a protein, a receptor, an antibody, an antigen, a drug, virus, nucleic acid, a polysaccharide or a metabolite.

In accordance with an aspect provided herein, an elastomeric negative contrast acoustic particle made according to the one or more methods disclosed herein is provided. The functional group is covalently modified with a moiety for binding to a target of interest.

In accordance with an aspect provided herein, the target of interest includes one of a cell, a protein, a receptor, an antibody, an antigen, a drug, virus, nucleic acid, a polysaccharide or a metabolite.

In accordance with an aspect provided herein, a method for acoustic-mediated bioanalysis is provided. The method includes exposing a fluid sample suspected of containing a target of interest to a plurality of elastomeric negative contrast acoustic particles disclosed herein. The functional group of the particles includes a covalently attached moiety for binding to the target of interest, under conditions sufficient that the moiety binds to the target. The method includes subjecting the fluid sample to acoustic radiation pressure from an acoustic standing wave sufficient within an acoustic focusing chamber to focus the particles to the acoustic pressure antinodes such that the target is separated from other components in the sample.

In accordance with an aspect provided herein, the method includes removing any positive acoustic contrast particles from the acoustic focusing chamber.

In accordance with an aspect provided herein, the method includes removing the negative contrast acoustic particles from the acoustic focusing chamber and analyzing the particles.

In accordance with an aspect provided herein, a method for synthesizing elastomeric negative contrast acoustic particles having a covalently functionalized surfactant for recognition of a target of interest is provided. The method includes emulsifying an elastomer pre-polymer with a catalyst in the presence of a surfactant under conditions sufficient to produce emulsion droplets, wherein the surfactant is covalently functionalized to allow for binding to a target of interest, and curing the emulsion droplets under conditions sufficient to form stable elastomeric negative acoustic contrast particles having the functionalized surfactant available for binding to the target of interest.

In accordance with an aspect provided herein, the elastomer pre-polymer includes a silicone material.

In accordance with an aspect provided herein, the surfactant is functionalized with one of a vinyl, carboxylate, hydroxyl, epoxide, sulfhydryl, amide, acrylate, thiol, azide, maleimide, isocyanate, aziridine, carbonate, N-hydroxysuccinimide ester, imidoester, carbodiimide, anhydride, succinimidyl carbonate, and amine, and combinations thereof.

In accordance with an aspect provided herein, the elastomer pre-polymer includes polydimethylsiloxane (PDMS) or polyvinylmethylsiloxane (PVMS).

In accordance with an aspect provided herein, the surfactant is a nonionic surfactant including one of PLURONIC F108, PLURONIC F68, PLURONIC P103, PLURONIC F98, PLURONIC P84, PLURONIC F127, PLURONIC F88, PLURONIC F77, PLURONIC P84, and FIOS, and combinations thereof, or an ionic surfactant including one of CHAPS, betaines, lecithin, phosphates, cetyl trimethylammonium bromide (CTAB), hexadecyl trimethyl ammonium bromide, cetyl trimethylammonium chloride (CTAC), cetylpyridinium chloride (CPC), benzalkonium chloride (BAC), Benzethonium chloride (BZT), ammonium lauryl sulfate, and sodium lauryl sulfate, and combinations thereof.

In accordance with an aspect provided herein, the nonionic surfactant includes a PLURONIC surfactant having greater than 50 end groups of polyethylene oxide (PEO).

In accordance with an aspect provided herein, the nonionic surfactant includes a triblock copolymer surfactant having a hydrophile-lipophile (HLB) value greater than 24.

In accordance with an aspect provided herein, the functionalized surfactant includes a linking target that binds to the target of interest.

In accordance with an aspect provided herein, the linking target is one of a biotin, a biotinylated tetrafluorophenyl azide, a streptavidin, a fluorescent streptavidin, nucleic acid, an antibody, or an antigen.

In accordance with an aspect provided herein, the target of interest includes one of a cell, a protein, a receptor, an antibody, an antigen, a drug, polysaccharide, or a metabolite.

In accordance with an aspect provided herein, the elastomeric negative contrast acoustic particle is functionalized such that binds to the target of interest.

In accordance with an aspect provided herein, an elastomeric negative contrast acoustic particle made according to any of the methods provided herein is disclosed.

In accordance with an aspect provided herein, the target of interest of the elastomeric negative contrast acoustic particle includes one of a cell, a protein, a receptor, an antibody, an antigen, a drug, a virus, a nucleic acid, a polysaccharide, or a metabolite.

In accordance with an aspect provided herein, a method for acoustic-mediated bioanalysis is provided. The method includes exposing a fluid sample suspected of containing a target of interest to a plurality of elastomeric negative contrast acoustic particles under conditions sufficient that the functionalized surfactant binds to the target of interest, and subjecting the fluid sample to acoustic radiation pressure from an acoustic standing wave sufficient within an acoustic focusing chamber to focus the particles to the acoustic pressure antinodes such that the target is separated from other components in the sample.

In accordance with an aspect provided herein, the method includes removing any positive acoustic contrast particles from the acoustic focusing chamber.

In accordance with an aspect provided herein, the method includes removing the negative contrast acoustic particles from the acoustic focusing chamber and analyzing the particles.

In accordance with an aspect provided herein, a method for bulk synthesis of monodisperse, tunable contrast acoustic particles is provided. The method includes agitating varying ratios of one of a di-functional, a tri-functional, and a tetra-functional siloxane monomer in an aqueous solution such that hydrolysis and uniform condensation occur upon addition of a catalyst and monodisperse acoustic contrast particles are formed. The tunable acoustic contrast of the monodisperse particles formed is based on the ratios of the di-functional, tri-functional, and tetra-functional siloxane monomers used.

In accordance with an aspect provided herein, the siloxane monomer includes a conjugative group such that the group is available for covalent modification in the formed monodisperse particles.

In accordance with an aspect provided herein, the conjugative group includes a vinyl, carboxylate, hydroxyl, epoxide, sulfhydryl, amide, acrylate, thiol, or amine.

In accordance with an aspect provided herein, the conjugative group includes a vinyl group.

In accordance with an aspect provided herein, the method includes a co-solvent for miscibility.

In accordance with an aspect provided herein, the co-solvent is ethanol.

In accordance with an aspect provided herein, the ratio of the co-solvent to water ranges between about 1:100 and 50:50.

In accordance with an aspect provided herein, the method includes washing the particles.

In accordance with an aspect provided herein, the method includes heating the solution to about 70° C. such that produced alcohol groups are boiled out of solution.

In accordance with an aspect provided herein, the ratio of the di-functional to the tri-functional siloxane monomer is one of 0:100, about 25:75, about 50:50, or about 75:25.

In accordance with an aspect provided herein, the di-functional monomer is a dimethoxydimethylsilane (DMODMS) or a vinylmethyldimethoxysilane (VMDMOS).

In accordance with an aspect provided herein, the tri-functional monomer is a trimethoxymethylsilane (TMOMS) or a vinyltrimethoxysilane (VTMOS).

In accordance with an aspect provided herein, the catalyst is ammonium hydroxide.

In accordance with an aspect provided herein, the monodisperse particles range in size from about 100 nm to about 800 nm.

In accordance with an aspect provided herein, a monodisperse, acoustic contrast particle made according to one or more methods disclosed herein is provided.

In accordance with an aspect provided herein, a monodisperse, acoustic contrast particle has a conjugative group that is covalently modified with a moiety for binding to a target of interest.

In accordance with an aspect provided herein, the target of interest of the particle includes one of a cell, a protein, a receptor, an antibody, a virus, an antigen, a drug, and a metabolite.

In accordance with an aspect provided herein, a method for acoustic-mediated bioanalysis is provided. The method includes exposing a fluid sample suspected of containing a target of interest to a plurality of acoustic contrast particles according to claim 48 under conditions sufficient that the moiety binds to the target, and subjecting the fluid sample to acoustic radiation pressure from an acoustic standing wave sufficient within an acoustic focusing chamber to focus the particles to the acoustic antinodes such that the target is separated from other components in the sample.

In accordance with an aspect provided herein, a method for bulk synthesis of monodisperse, tunable contrast acoustic particles is provided. The method includes agitating in an acidic aqueous solution varying ratios of one of a di-functional, a tri-functional, and a tetra-functional siloxane monomer under conditions sufficient to allow for hydrolysis and the formation of oligomers, and adding a catalyst and continuing to agitate the solution under alkaline pH conditions sufficient to allow for a condensation reaction and formation of monodisperse acoustic contrast particles. The tunable acoustic contrast of the monodisperse particles formed is based on the ratios of the di-functional, tri-functional, and tetra-functional siloxane monomers used.

In accordance with an aspect provided herein, the siloxane monomer includes a conjugative group such that the group is available for covalent modification in the formed monodisperse particles.

In accordance with an aspect provided herein, the conjugative group includes a vinyl, carboxylate, hydroxyl, epoxide, sulfhydryl, amide, acrylate, thiol, or amine.

In accordance with an aspect provided herein, the conjugative group includes a vinyl group.

In accordance with an aspect provided herein, the method includes washing the particles.

In accordance with an aspect provided herein, the method includes heating the solution to about 150° C. for a length of time sufficient to harden the particles.

In accordance with an aspect provided herein, the ratio of the tetra-functional to the di-functional siloxane monomer is one of 1:100, about 1:10, about 1:20, or about 1:4.

In accordance with an aspect provided herein, the di-functional siloxane monomer is a dimethoxydimethylsilane (DMODMS) or a vinylmethyldimethoxysilane (VMDMOS).

In accordance with an aspect provided herein, the tri-functional siloxane monomer is a trimethoxymethylsilane (TMOMS) or a vinyltrimethoxysilane (VTMOS).

In accordance with an aspect provided herein, the tetra-functional siloxane monomer is a trimethoxysilane (TMOS) or a (3-Aminopropyl)trimethoxysilane (AmTMOS).

In accordance with an aspect provided herein, the catalyst is ammonium hydroxide.

In accordance with an aspect provided herein, the monodisperse particles range in size from about 0.5 µm to about 5 µm.

In accordance with an aspect provided herein, a monodisperse, acoustic contrast particle made according to the one or more methods disclosed herein is provided.

In accordance with an aspect provided herein, the conjugative group is covalently modified with a moiety for binding to a target of interest.

In accordance with an aspect provided herein, the target of interest includes one of a cell, a protein, a virus, a receptor, an antibody, an antigen, a drug, and a metabolite.

In accordance with an aspect provided herein, a method for acoustic-mediated bioanalysis is provided. The method includes exposing a fluid sample suspected of containing a target of interest to a plurality of acoustic contrast particles according to claim 65 under conditions sufficient that the moiety binds to the target and subjecting the fluid sample to acoustic radiation pressure from an acoustic standing wave sufficient within an acoustic focusing chamber to focus the particles to the acoustic antinodes such that the target is separated from other components in the sample.

In accordance with an aspect provided herein, a method for synthesizing monodisperse, tunable contrast acoustic particles is provided. The method includes agitating in an acidic aqueous solution varying ratios of one of a di-functional, a tri-functional, and a tetra-functional siloxane monomer under conditions sufficient to allow for hydrolysis and the formation of oligomers. The method may include removing a majority of the large non-uniform oligomers from the smaller hydrolyzed oligomers and adding a catalyst and continuing to agitate the solution under conditions sufficient to allow for a uniform condensation reaction and formation of monodisperse acoustic contrast particles. The tunable acoustic contrast of the monodisperse particles formed is based on the ratios of the di-functional, tri-functional, and tetra-functional siloxane monomers used.

In accordance with an aspect provided herein, the siloxane monomer includes a conjugative group such that the group is available for covalent modification in the formed monodisperse particles.

In accordance with an aspect provided herein, the conjugative group includes a vinyl, carboxylate, hydroxyl, epoxide, sulfhydryl, amide, acrylate, thiol, or amine.

In accordance with an aspect provided herein, the conjugative group includes a vinyl group.

In accordance with an aspect provided herein, the method includes washing the particles.

In accordance with an aspect provided herein, the method includes sonicating the particles.

In accordance with an aspect provided herein, the particles are sonicated in ethanol.

In accordance with an aspect provided herein, the acidic aqueous solution is less than pH3.

In accordance with an aspect provided herein, the method is performed with only the tetra-functional siloxane monomer.

In accordance with an aspect provided herein, the di-functional siloxane monomer is a dimethoxydimethylsilane (DMODMS) or a vinylmethyldimethoxysilane (VMDMOS).

In accordance with an aspect provided herein, the tri-functional siloxane monomer is a trimethoxymethylsilane (TMOMS) or a vinyltrimethoxysilane (VTMOS).

In accordance with an aspect provided herein, the tetra-functional siloxane monomer is a trimethoxysilane (TMOS).

In accordance with an aspect provided herein, the catalyst is triethylamine.

In accordance with an aspect provided herein, the monodisperse particles range in size from about 0.5 µm to about 50 µm.

In accordance with an aspect provided herein, the conjugative group is covalently modified with a moiety for binding to a target of interest.

In accordance with an aspect provided herein, the target of interest includes one of a cell, a protein, a receptor, a virus, an antibody, an antigen, a drug, a polysaccharide or a metabolite.

In accordance with an aspect provided herein, a method for acoustic-mediated bioanalysis is provided. The method includes exposing a fluid sample suspected of containing a target of interest to a plurality of acoustic contrast particles according to claim 83 under conditions sufficient that the moiety binds to the target and subjecting the fluid sample to acoustic radiation pressure sufficient from an acoustic standing wave within an acoustic focusing chamber to focus the particles to the acoustic antinodes such that the target is separated from other components in the sample.

In accordance with an aspect provided herein, a method for synthesizing monodisperse, tunable contrast acoustic particles is provided. The method includes agitating in an acidic aqueous solution varying ratios of one of a tri-functional and a tetra-functional siloxane monomer under conditions sufficient to allow for hydrolysis and the formation of oligomers, agitating in a separate acidic aqueous solution one or more of a di-functional siloxane monomer and under conditions sufficient to allow for hydrolysis and the formation of oligomers, removing from the di-functional solution a majority of the large non-uniform oligomers from the smaller hydrolyzed oligomers, adding a catalyst for uniform condensation, and continuing to agitate the solution, and removing from the tri- and tetra-functional solution a majority of the large non-uniform oligomers from the smaller hydrolyzed oligomers, adding the tri- and tetra-functional solution directly to the di-functional solution, adding a catalyst and continuing to agitate the solution under conditions sufficient to allow for a condensation reaction and formation of monodisperse acoustic contrast particles. The tunable acoustic contrast of the monodisperse particles formed is based on the ratios of the di-functional, tri-functional, and tetra-functional siloxane monomers used.

In accordance with an aspect provided herein, the siloxane monomer includes a conjugative group such that the group is available for covalent modification in the formed monodisperse particles.

In accordance with an aspect provided herein, the conjugative group includes a vinyl, carboxylate, hydroxyl, epoxide, sulfhydryl, amide, acrylate, thiol, or amine.

In accordance with an aspect provided herein, the conjugative group includes a vinyl group.

In accordance with an aspect provided herein, the di-functional siloxane monomer is a dimethoxydimethylsilane (DMODMS) or a vinylmethyldimethoxysilane (VMDMOS).

In accordance with an aspect provided herein, the tri-functional siloxane monomer is a trimethoxymethylsilane (TMOMS) or a vinyltrimethoxysilane (VTMOS).

In accordance with an aspect provided herein, the tetra-functional siloxane monomer is a trimethoxysilane (TMOS).

In accordance with an aspect provided herein, the catalyst is triethylamine.

In accordance with an aspect provided herein, the monodisperse particles range in size from about 0.5 μm to about 10 μm.

In accordance with an aspect provided herein, the conjugative group is covalently modified with a moiety for binding to a target of interest.

In accordance with an aspect provided herein, the target of interest includes one of a cell, a protein, a receptor, a virus, an antibody, an antigen, a drug, a polysaccharide or a metabolite.

In accordance with an aspect provided herein, a method for acoustic-mediated bioanalysis is provided. The method includes exposing a fluid sample suspected of containing a target of interest to a plurality of acoustic contrast particles according to claim 97 under conditions sufficient that the moiety binds to the target and subjecting the fluid sample to acoustic radiation pressure from an acoustic standing wave sufficient within an acoustic focusing chamber to focus the particles to their acoustic antinodes such that the target is separated from other components in the sample.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Example 1

Methods for Synthesis of FMAR Colloids using Nucleation and Growth

Described below are four distinct approaches (Protocols I, II, III, and IV) for synthesizing FMAR colloids from nucleation and growth. In general, colloid particles were prepared using a vinyl-siloxane such as, for example, to list a few vinyltrimethoxysilane, triethoxyvinylsilane, vinylmethyldiethoxysilane, and vinylmethyldimethoxysilane. The vinyl-siloxane was added to acidic aqueous solution and agitated (e.g., stirred, vortexed, sonicated) to permit hydrolysis. During this step other siloxanes may be added such as, for example, to list a few tetramethylorthosilicate, methyltrimethoxysilane, and dimethoxydimethylsilane. At this point, a catalyst was added to begin the condensation reaction and formation of monodisperse particles. In another example, vinyl-siloxanes such as, for example, to list a few vinyltrimethoxysilane, triethoxyvinylsilane, vinylmethyldiethoxysilane, and vinylmethyldimethoxysilane and other siloxanes such as, for example, to list a few tetramethylorthosilicate, methyltrimethoxysilane, and dimethoxydimethylsilane were added to a mixture of water and co-solvent. At this point, a catalyst was added and the mixture was agitated. A variety of modifications may be made to this nucleation and growth protocol such as altering the temperature, resuspending in a non-reactive medium, or adding surfactant to increase particle stability.

Fabrication of acoustofluidic device. An acoustofluidic device or otherwise referred to as an acoustic focusing chamber was prepared to characterize the FMARs. The acoustofluidic device was prepared using standard photolithography, deep reactive-ion etching (DRIE), anodic bonding and plasma bonding. The device contained a downstream collection module and an acoustic actuation component (i.e., lead zirconate titanate piezoelectric element or PZT). The channel width was designed to operate at a half wavelength resonant mode (e.g., 252 μm and driving frequency of 2.94 MHz or 272 μm and 2.72 MHz) resulting in an antinode at both channel walls and a single node in the channel center line. For the experiments, an electric signal with peak-to-peak voltage of 31V is applied to the PZT.

Each Protocol for synthesizing the FMARs is now described in further detail below containing a list of materials, methods, and representative results for each of the types of colloids produced.

Generalized Materials List
    Di-functional species:
        Dimethoxydimethylsilane (DMODMS)
        Vinylmethyldimethoxysilane (VMDMOS)
        Vinylmethyldiethoxysilane (VMDEOS)
        3-Aminopropyl(diethoxy)methylsilane (AmDEOMS)
        Any other di-functional siloxane monomer containing at least one functional group
    Tri-functional species:
        Trimethoxymethylsilane (TMOMS)
        Vinyltrimethoxysilane (VTMOS)
        Triethoxyvinylsilane (VTEOS)
        (3-Aminopropyl)trimethoxysilane (AmTMOS)
        3-(Trimethoxysilyl)propylacrylate (AcTMOS)
        [3-(Diethylamino)propyl]trimethoxysilane (DAmTMOS)
        Any other tri-functional siloxane monomer containing at least one functional group
    Tetra-functional species:
        Tetraethylorthosilicate (TEOS)
        Tetramethoxysilane (TMOS)
        Tetrapropylorthosilicate (TPOS)
    Catalyst:
        Ammonium ($NH_4OH$)
        Tin octoate
        Triethylamine (TEA)
    Co-Solvent:
        Ethanol (EtOH)
        Methanol
        Polysorbate
        Polyethylene glycol
        Sodium dodecyl sulfate (SDS)
    Acid: Hydrochloric acid (HCl)
        Any other acid Protocol I (Stöber-Based Method)

This approach employs fundamental features from the Stöber method (Stöber, W. & Fink, A. (1969). However, two distinct features that make the method disclosed herein different are 1) the ratios of the di-, tri-, and tetra-functional monomers incorporated, which results in colloids having various cross-linking densities and bulk moduli useful for various acoustic behaviors, and 2) the colloids that are synthesized contain many functional groups.

Materials
Di-functional specie(s)
Tri-functional specie(s)
Tetra-functional specie(s)
Catalyst
Co-solvent Methods
1. Mix 4 mL co-solvent and 4.5 mL DI $H_2O$ (or smaller ratios of co-solvent:DI $H_2O$ for slower reactions)
2. Add varying ratios of di-, tri-, and tetra-functional species that equal to 100 µL
3. Pipette 1 mL catalyst
4. Vigorously agitate via shaking or mixing
5. Place on a hot plate at 70° C. (optional)

Figure 2:
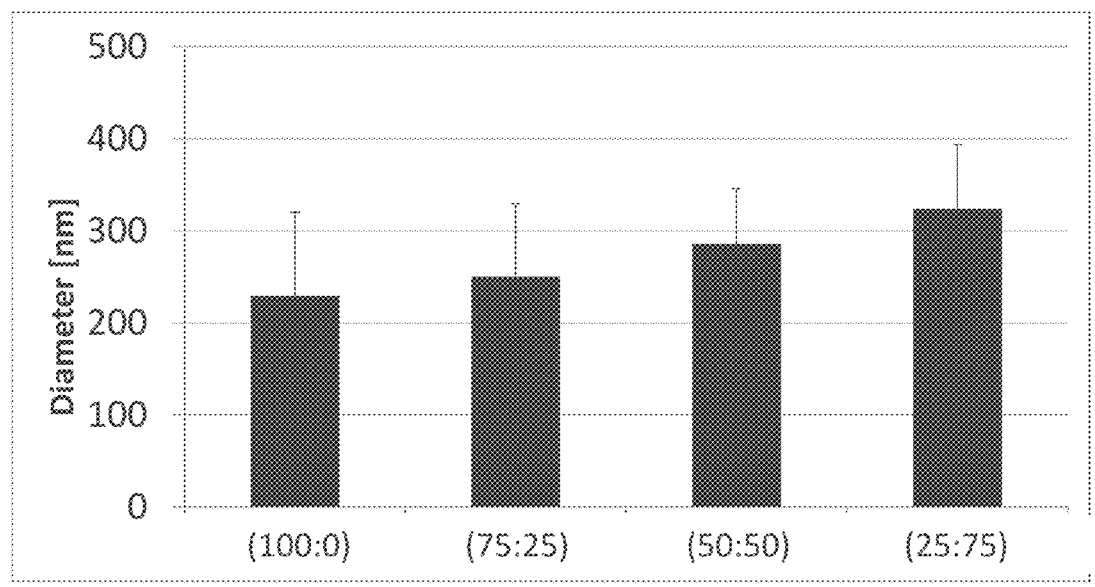
FIG. 2 is a graph showing relative colloid size of particles made using Protocol I according to one or more embodiments of the present disclosure. The FMAR particles were synthesized with reproducible and tunable size ranges that extend beyond 100 to 800 nm measured by dynamic light scattering (DLS). The ratios shown on the x axis represent the ratio of tri-functional monomers (vinyltrimethoxysilane (VTMOS)) to di-functional monomers (vinylmethyldimethoxysilane (VMDMOS)) used in the preparation of the colloids represented by each bar, providing ample vinyl groups on the surface of synthesized particles for facile conjugation reactions.

Results
Colloids of varying compressibilities were produce with this Protocol having diameters on the order of 100-800 nm within minutes after the addition of a catalyst-Note: colloid size and compressibility depends on monomer ratio, monomer concentration, hydrolysis time, and catalyst strength. For example, FIG. 2 is a graph showing relative colloid size of particles made using Protocol I. The particles were synthesized with reproducible and tunable size ranges that extend beyond 100 to 800 nm measured by dynamic light scattering (DLS). The ratios shown on the x axis represent the ratio of tri-functional monomers (vinyltrimethoxysilane (VTMOS)) to di-functional monomers (vinylmethyldimethoxysilane (VMDMOS)) used in the preparation of the colloids represented by each bar. The particles in FIGS. 2-4 were produced specifically according to Protocol I as follows:

Materials
    Di-functional species "silica initiator"
        Dimethoxydimethylsilane (DMODMS)
        Vinylmethyldimethoxysilane (VMDMOS)
    Tri-functional species "silica cross-linker"
        Trimethoxymethylsilane (TMOMS)
        Vinyltrimethoxysilane (VTMOS)
    Catalyst:
        i.e., Ammonia 880 ($NH_4OH$)
    Co-Solvent:
        i.e., 200-proof ethanol (EtOH)

Methods
Mix 4 mL EtOH and 4.65 mL DI $H_2O$ in 20 mL glass vial (or 100 µL EtOH and 8.55 mL DI $H_2O$ for slower reactions)
1. Add 50 µL di-functional species and 50 µL tri-functional species
    OR 25 µL di-functional species and 75 µL tri-functional species
    OR 75 µL di-functional species and 25 µL tri-functional species
    OR 100 µL tri-functional species
2. Pipette 1 mL $NH_4OH$
3. Shake for 30 min with a vortex speed of 4
4. Place on a hot plate at 70° C. to boil out produced methanol and keep ethanol (optional)
    This protocol produces semi-incompressible colloids with diameters on the order of 100-800 nm within minutes after the addition of a catalyst (or hours if following parenthetical option in methods step 1)

Figure 3:
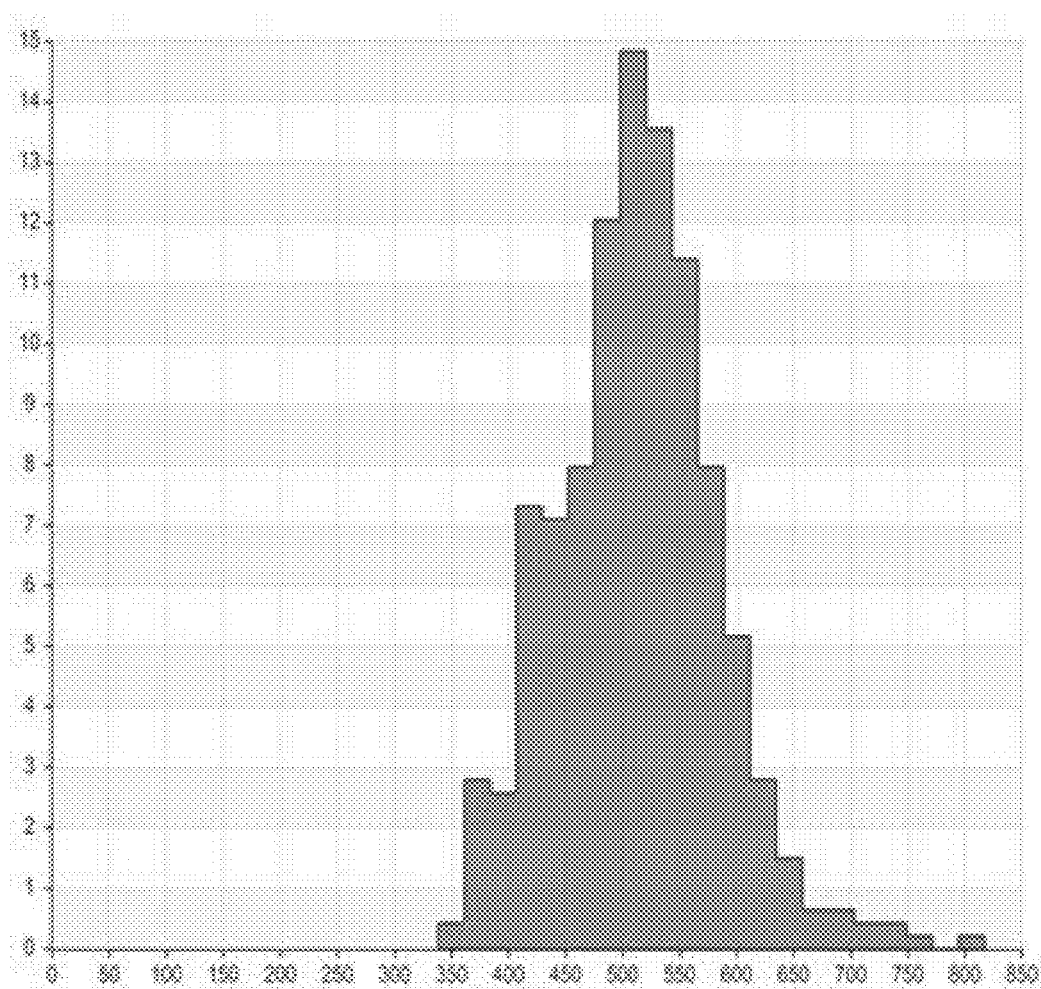
FIG. 3 is a graph showing size distribution of FMAR colloids made using Protocol I with different mixing conditions according to one or more embodiments of the present disclosure. Particles were made using the siloxane monomer trimethoxymethylsilane (TMOMS). Particle diameter (nm) is shown on the x axis and percent population by count is shown on the y axis. Average size measured by a qNANO instrument was 496.2 nm and the coefficient of variance was 12.65%.

FIG. 3 is a graph showing size distribution of colloids made using Protocol I with different mixing conditions according to one or more embodiments of the present disclosure. Particles were made using the siloxane monomer trimethoxymethylsilane (TMOMS). Particle diameter (nm) is shown on the x axis and percent population by count is shown on the y axis. Average size measured by a qNANO instrument was 496.2 nm and the coefficient of variance was 12.65%.

Figure 4A:
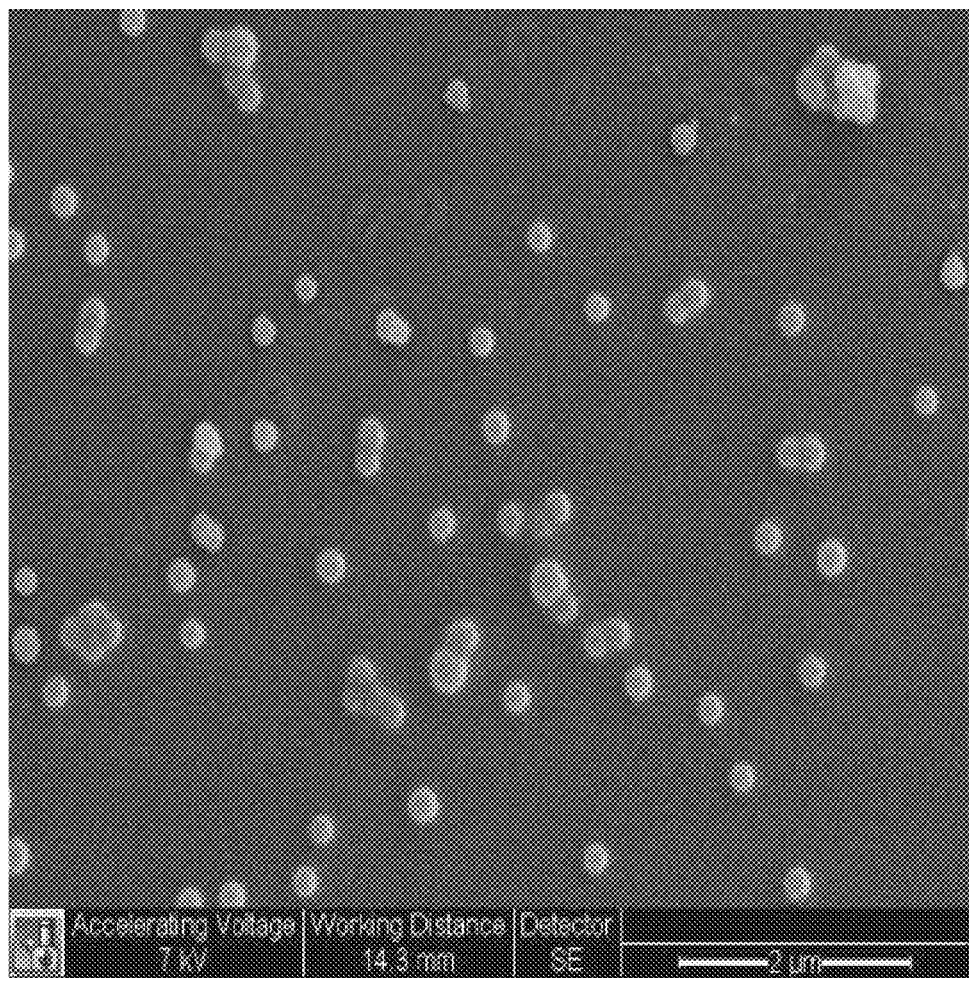
FIGS. 4A & 4B are images of particles made using Protocol I according to one or more embodiments of the present disclosure. Particles were made using the siloxane monomer vinyltrimethoxysilane (VTMOS). A) Scanning electron micrograph (SEM) image. B) Optical microscope image.
Figure 4B:
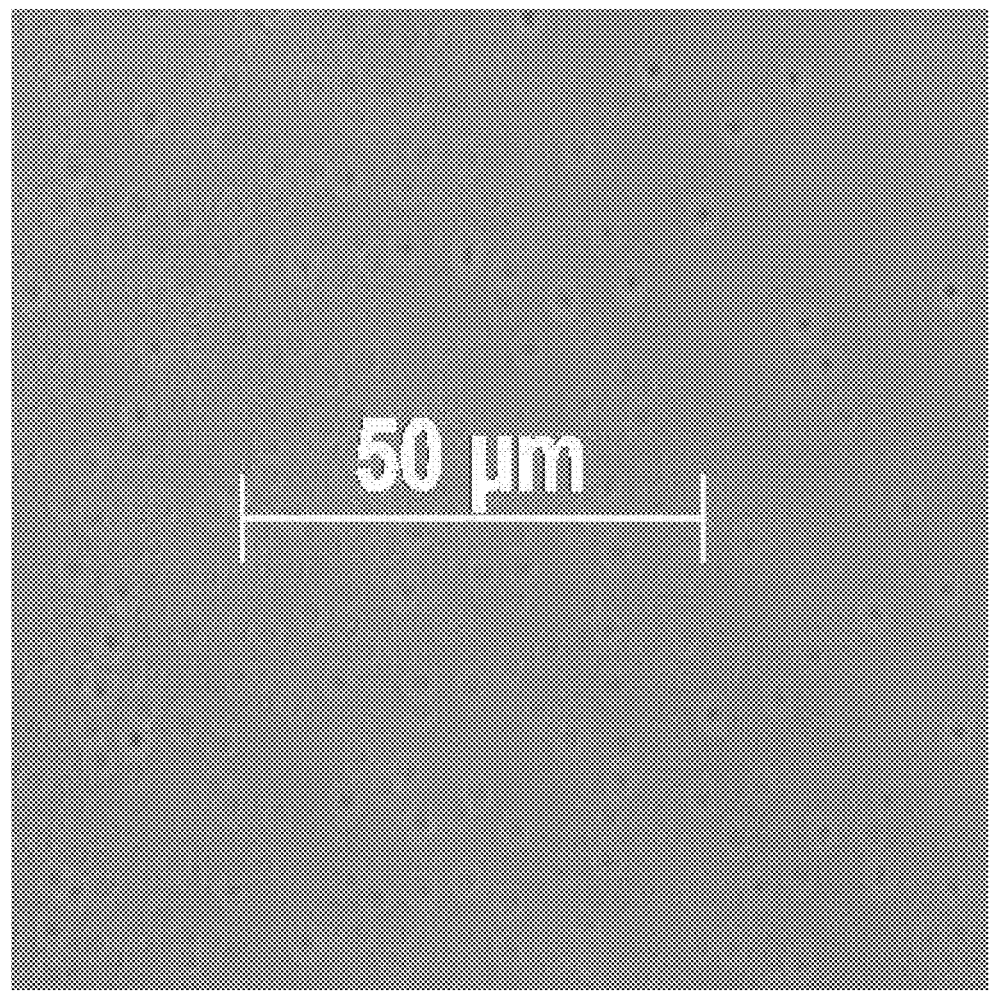

FIGS. 4A & 4B are images of particles made using Protocol I according to one or more embodiments of the present disclosure. Particles were made using the siloxane monomer vinyltrimethoxysilane (VTMOS). A) Scanning electron micrograph (SEM) image. B) Optical microscope image.

Protocol II (Acidic Hydrolysis Method)

This protocol is distinct from the previous method due to the variation in the synthesis procedure, which affects the nature of the microparticles produced. Here, functional siloxane monomers are hydrolyzed in a low pH medium and polycondensated in a high pH medium instead of hydrolyzing and polycondensating in the same high pH medium. These particles are also stable, monodisperse, functional, and acoustically active.

Materials
Di-functional specie(s)
Tri-functional specie(s)
Tetra-functional specie(s)
Catalyst
Acid Methods
1. Dilute concentrated stock HCl or other strong acid (dilutions will range)
2. Dilute concentrated stock $NH_4OH$ or other catalyst (dilutions will range)
3. Add varying ratios of di-, tri-, and tetra-functional species that equal 1.25 mL to 7.5 mL DI $H_2O$
4. Keep at 4° C. (optional)
5. Add 5 µL diluted HCl or other strong acid
6. Vigorously stir or mix solution for 5 hrs
7. Add 500 µL diluted catalyst and continue stirring for 10 min
8. Wash particles and resuspend in a stable solution
9. Heat to 150° C. for 12 hrs (optional)

Figure 6:
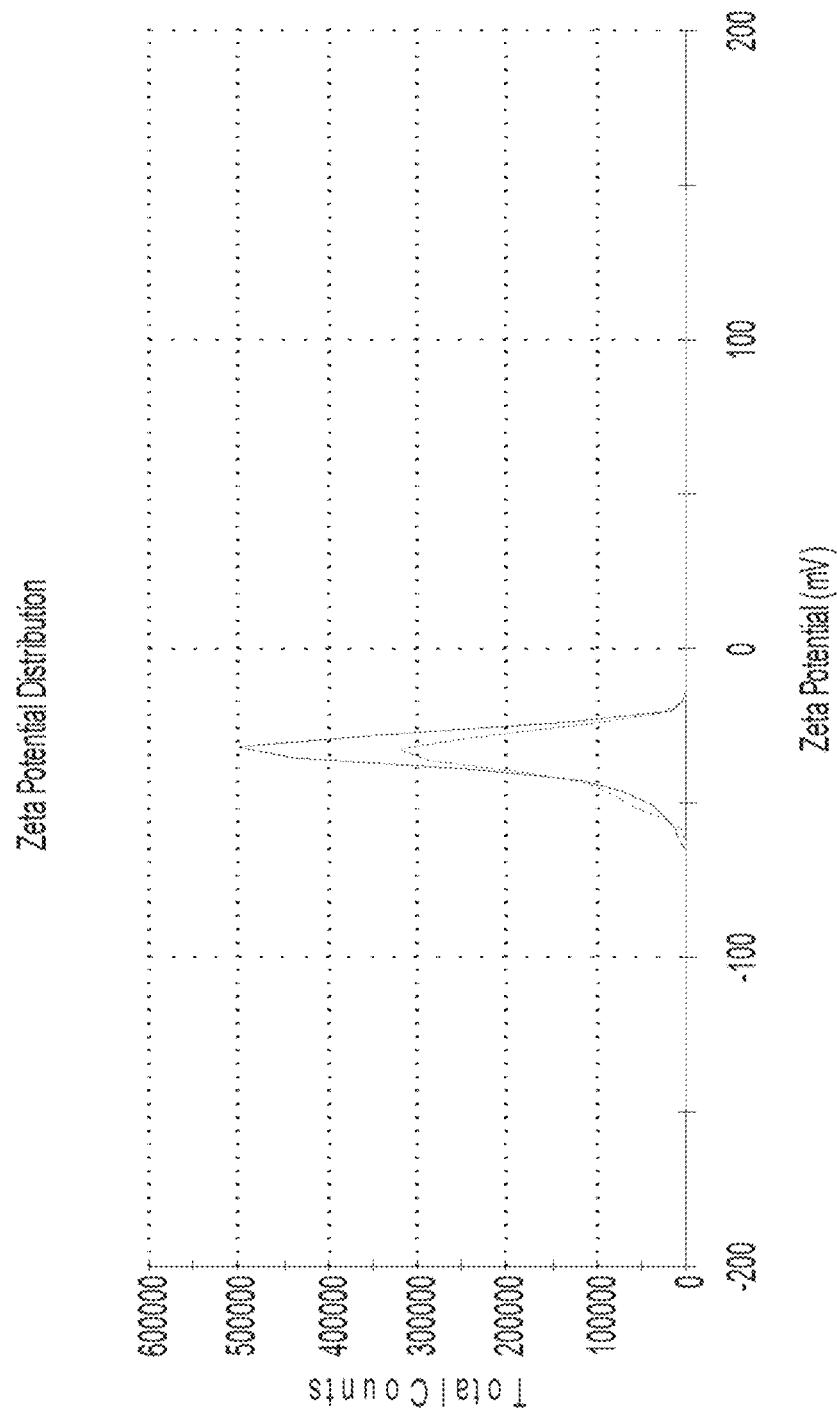
FIG. 6 is a graph of Zeta Potential of particles described in FIG. 5A-5B made via Protocol II using all tri-functional species trimethoxymethylsilane (TMOMS). The surface charge indicates that the colloids are sufficiently stable without the use of protective surfactants.
Figure 7:
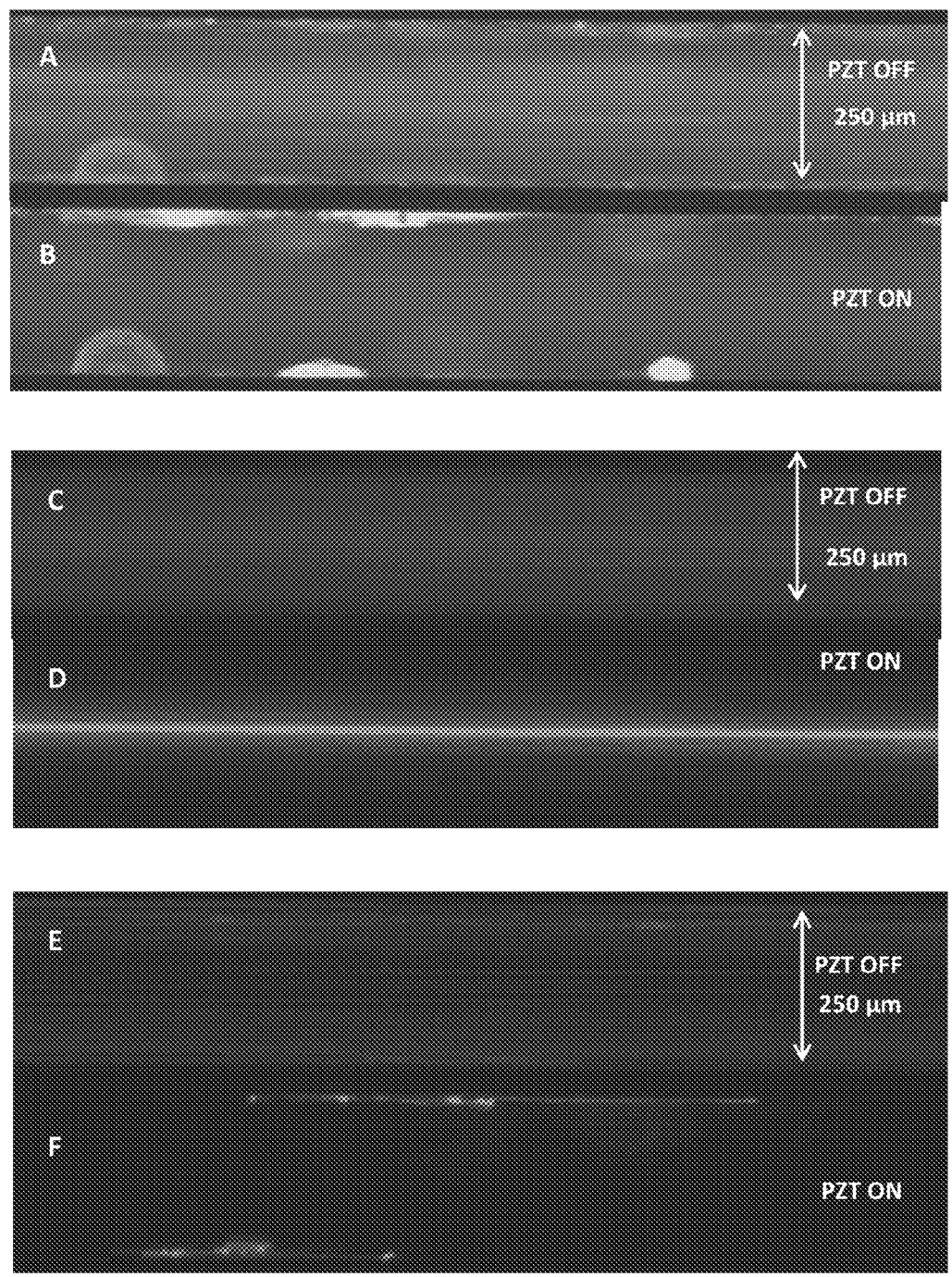
FIGS. 7A-7F are fluorescent images of FMAR colloids (1:100 monomer ratio of Tetramethoxysilane (TMOS):Dimethoxydimethylsilane (DMODMS) siloxane monomers) made via Protocol II with negative acoustic contrast in a silicon acoustofluidic chip as a demonstration that the FMAR colloids are sufficient to displace positive acoustic contrast particles from the acoustic node to the acoustic antinodes according to one or more embodiments of the present disclosure. A) Streptavidin-conjugated ALEXA FLUOR 488 incubated FMAR colloids as a positive control (PZT power=0V, flow=15 µL/min). B) The same particles as in (A) (PZT power=15V, flow=15 µL/min). C) Pink fluorescent biotin-coated polystyrene beads (PZT power=0V, flow=100 µL/min). D) Same particles as (C) (PZT power=15V, flow=100 µL/min). E) FMAR colloids bound to polystyrene beads used as a surrogate test (PZT power=0V, flow=100 µL/min). F) Same particles as (E) (PZT power=10V, flow=100 µL/min).
Figure 8A:
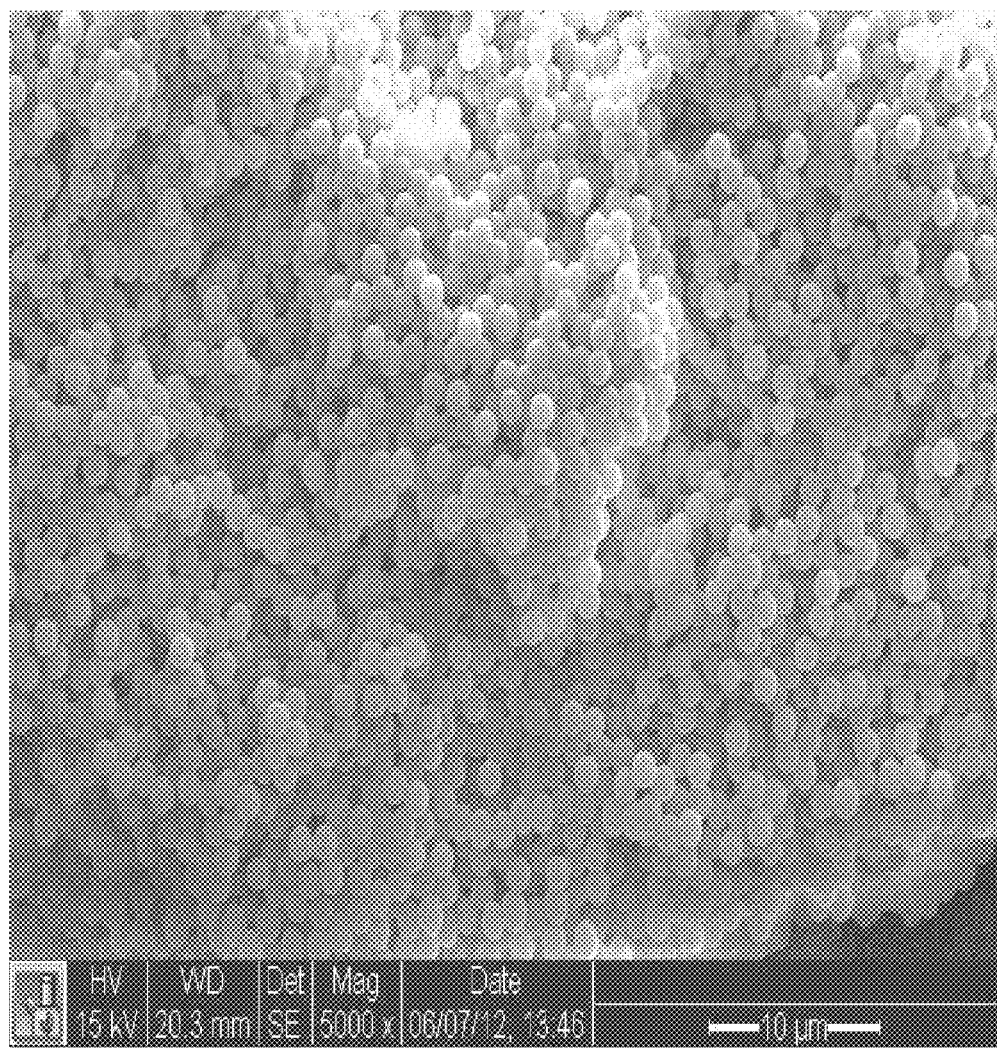
FIGS. 8A-8D are SEM images of colloids synthesized using Protocol III at various magnifications according to one or more embodiments of the present disclosure. FMAR colloids were synthesized via rapid bulk synthesis using the siloxane monomer trimethoxymethylsilane (TMOMS). A) Particles are shown at a magnification of 5000×. B) Particles are shown are shown at a magnification of 15000×. C) Particles are shown at a magnification of 15000× at a different site than shown in (B). D) Particles are shown at a magnification of 2500×.
Figure 8B:
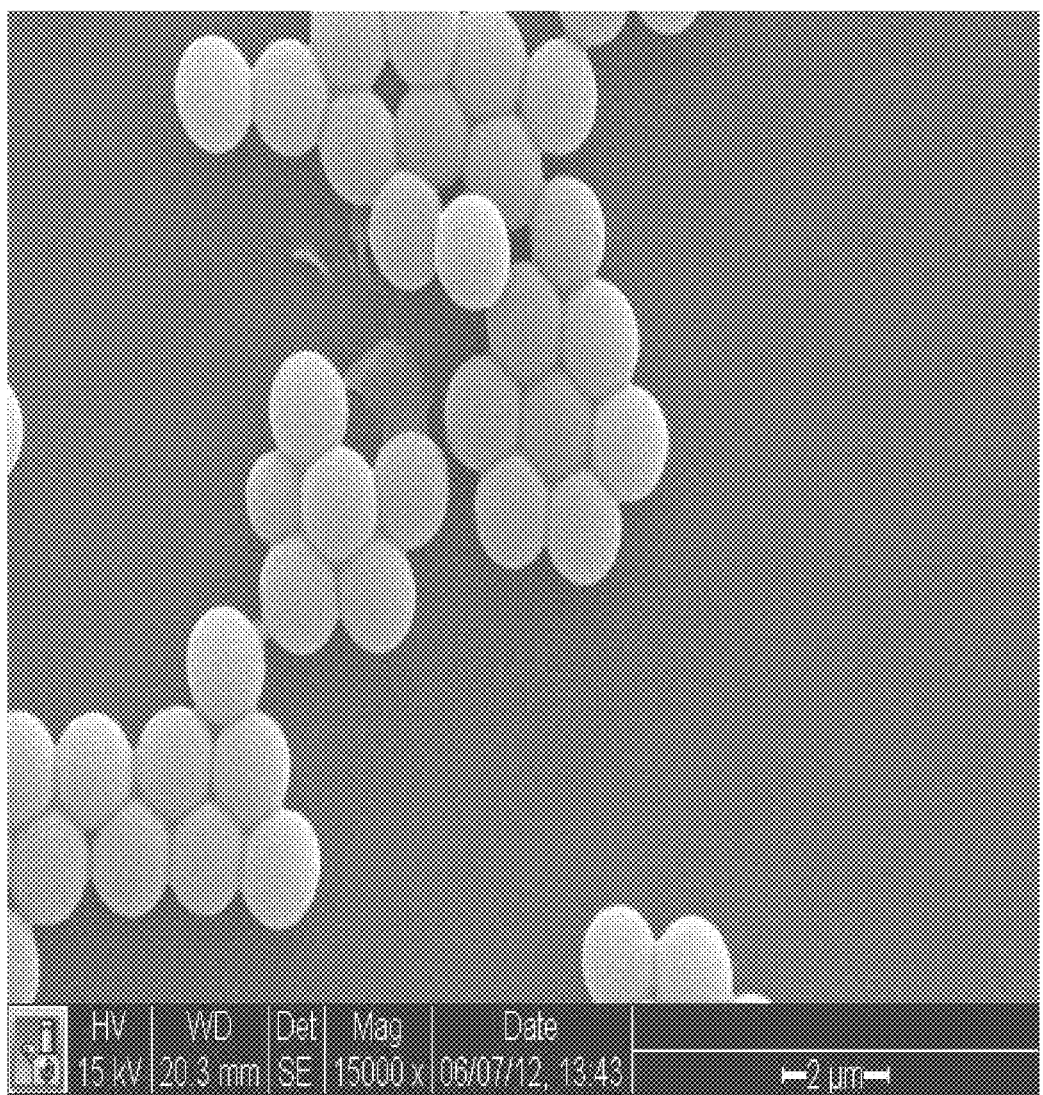
Figure 8C:
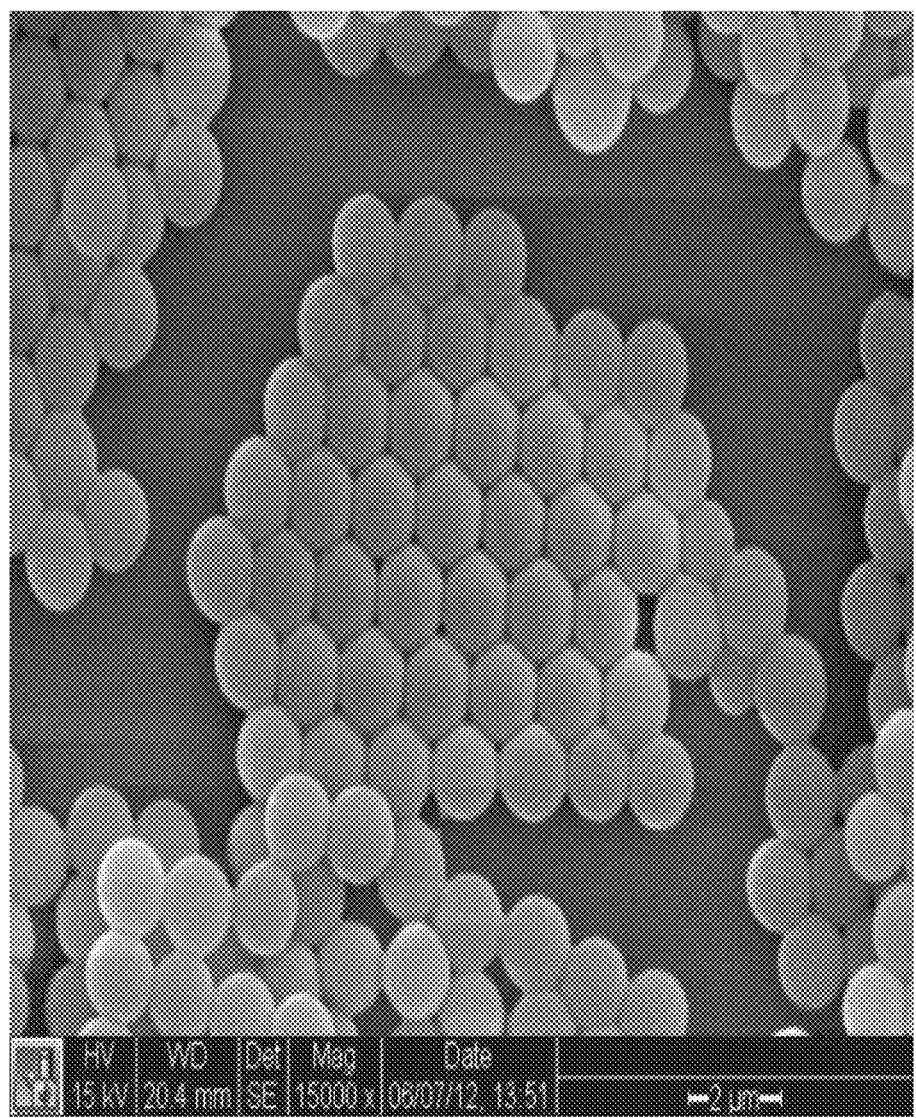
Figure 8D:
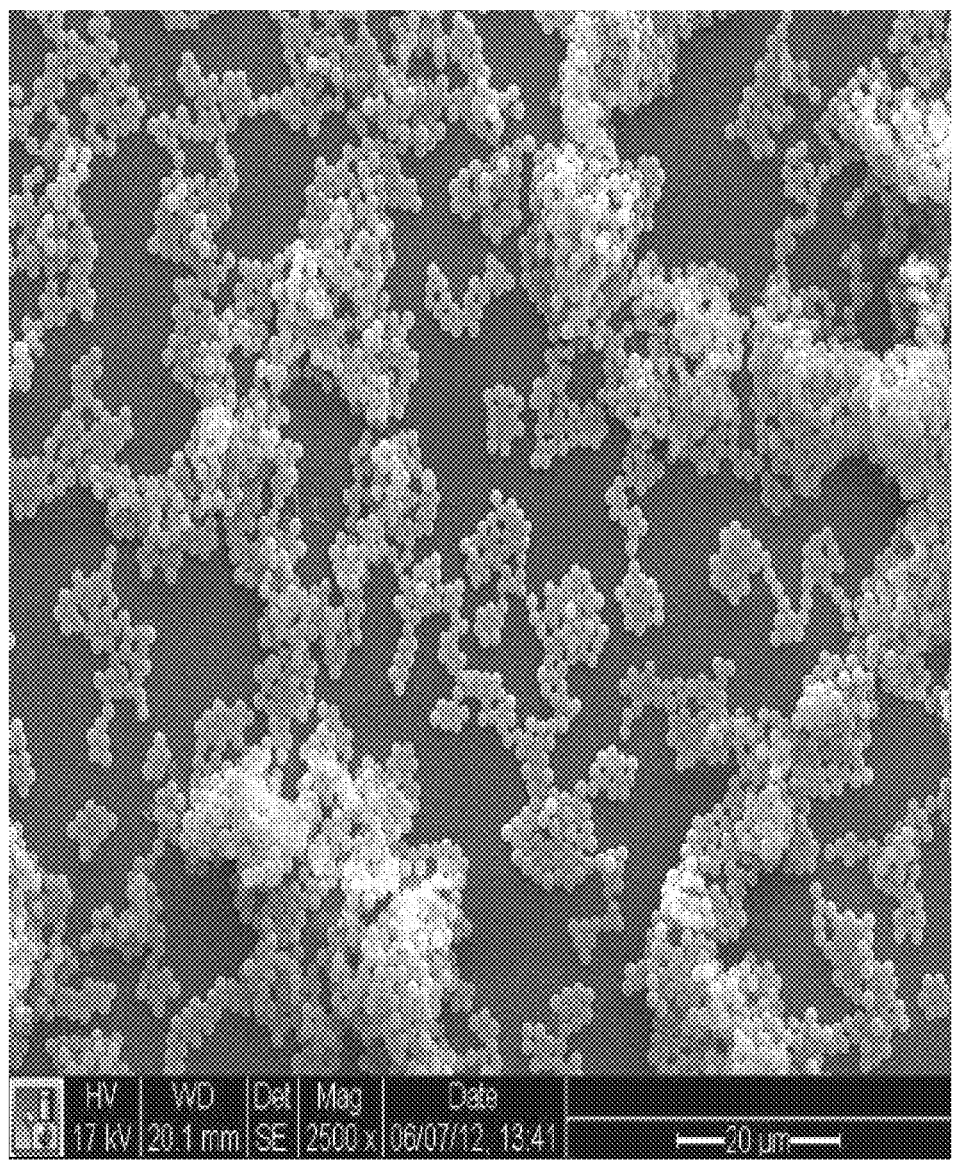

Results
Colloids produced using this method have varying compressibilities with diameters on the order of 0.5-5 µm several minutes after the addition of a catalyst. Colloid size and compressibility depends on monomer ratio, monomer concentration, hydrolysis time, and catalyst strength. Colloids produced using this method are shown in FIGS. 5-7. The colloids were produced specifically according to the following method.

| Reactants | Molar Ratio |
|---|---|
| Siloxane monomers (must add up to 1) | 1 |
| Tri-functional: | |
| Trimethoxymethylsilane (TMOMS) | |
| Vinyltrimethoxysilane (VTMOS) | |
| Di-functional: | |
| Dimethoxydimethylsilane (DMODMS) | |
| Vinylmethyldiethoxysilane (DMODMS) | |
| Tetra-functional: | |
| Trimethoxysilane (TMOS) | |
| Ammonia 880 ($NH_4OH$) | $7 \times 10^{-3}$ |
| Hydrochloric acid (37% in water, concentrated stock) | $5 \times 10^{-5}$ |
| DI water | 50 |

Methods
1. Dilute 50 μL 37% stock HCl solution into 5.254 mL DI H$_2$O to obtain 0.35% HCl
2. Dilute 50 μL 25% stock NH$_4$OH solution into 3.341 mL DI H$_2$O to obtain 0.37% NH$_3$
3. Add 1.366 mL TMOMS to 7.343 mL DI H$_2$O
   or 65.4 uL TMOS and 1.151 mL DMODMS (for a 1:100 ratio of tetra- to di-silicone)
   or 130.8 uL TMOS and 1.090 mL DMODMS (for a 1:10 ratio of tetra- to di-silicone)
   or 13.08 uL TMOS and 1.313 mL VMDMOS (for a 1:100 ratio of tetra- to di-vinyl)
   or 65.4 uL TMOS and 1.260 mL VMDMOS (for a 1:20 ratio of tetra- to di-vinyl)
   or 261.7 uL TMOS and 1.061 VMDMOS (for a 1:4 ratio of tetra- to di-vinyl)
   or 13.08 uL TMOS and 1.520 mL AmTMOS (for a 1:100 ratio of tetra- to di-amine)
4. Keep at 4° C. (optional)
5. Add 3.9 μL of 0.35% HCl
6. Vigorously stir for 5 hrs with a stir bar at 600 rpm
7. Add 646.7 μL of 0.37% NH$_4$OH and continue stirring for 4 hrs
8. Separate the particles from the suspension by centrifuging and resuspending in 1×PBS
9. Can harden particles by heating to 150° C. for 12 hours (optional)

Figure 5A:
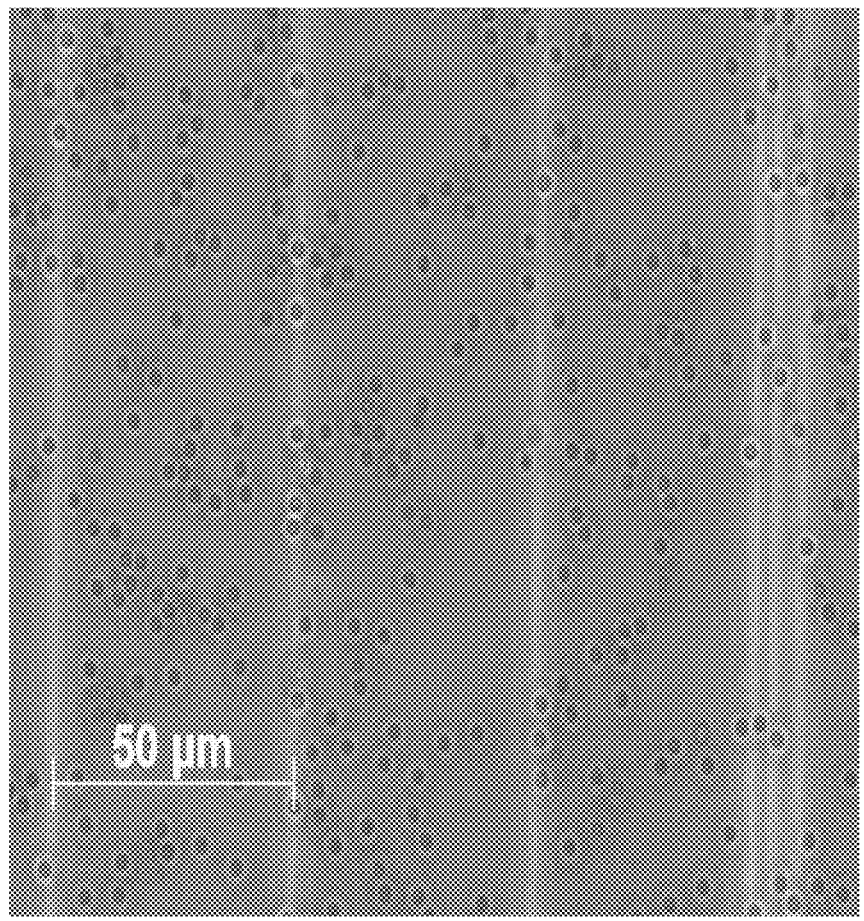
FIGS. 5A & 5B are optical micrographs of FMAR colloids made using the siloxane monomer trimethoxymethylsilane (TMOMS) as described in Protocol II. A) Particles are shown with microscope settings at a low (dark) plane of focusing. B) Particles are shown with microscope settings at a high (bright) plane of focusing. Both images show monodisperse colloids that do not aggregate without a surfactant.
Figure 5B:
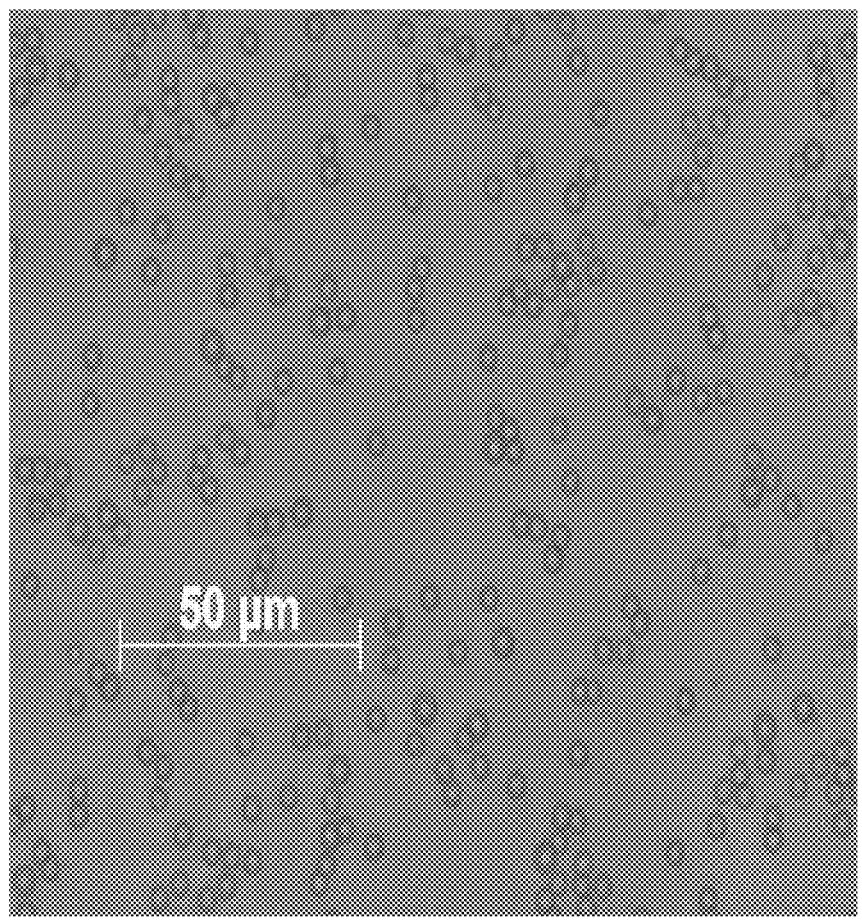

FIGS. 5A & 5B are optical micrographs of FMAR colloids made using the siloxane monomer trimethoxymethylsilane (TMOMS) as described in Protocol II. A) Particles are shown with microscope settings at a low (dark) plane of focusing. B) Particles are shown with microscope settings at a high (bright) plane of focusing. Both images show monodisperse colloids that do not aggregate without a surfactant.

FIG. 6 is a graph of Zeta Potential of particles described in FIG. 5A-5B made via Protocol II using all tri-functional species trimethoxymethylsilane (TMOMS). The surface charge indicates that the colloids are sufficiently stable without the use of protective surfactants.

FIGS. 7A-7F are fluorescent images of FMAR colloids (1:100 monomer ratio of Tetramethoxysilane (TMOS):Dimethoxydimethylsilane (DMODMS) siloxane monomers) made via Protocol II with negative acoustic contrast in a silicon acoustofluidic chip as a demonstration that the FMAR colloids are sufficient to displace positive acoustic contrast particles from the acoustic node to the acoustic antinodes according to one or more embodiments of the present disclosure. A) Streptavidin-conjugated ALEXA FLUOR 488 incubated FMAR colloids as a positive control (PZT power=1V, flow=15 μL/min). B) The same particles as in (A) (PZT power=15V, flow=15 μL/min). C) Pink fluorescent biotin-coated polystyrene beads (PZT power=0V, flow=100 μL/min). D) Same particles as (C) (PZT power=15V, flow=100 μL/min). E) FMAR colloids bound to polystyrene beads used as a surrogate test (PZT power=0V, flow=100 μL/min). F) Same particles as (E) (PZT power=10V, flow=100 μL/min).

Protocol III (Standard Nucleation & Growth Method)

The synthesis of colloids according to this Protocol III is distinct from the previous two Protocols because the functional siloxane monomers are hydrolyzed in a low pH medium for a short period of time (compared to Protocol II) and undergo size separation (typically through centrifugation) to remove large non-uniform oligomers from the hydrolyzed nuclei prior to the catalyst-induced polycondensation. The colloids that are produced using this method exhibit tight size uniformity and stability in suspensions like all methods described.

Materials
  Di-functional specie(s)
  Tri-functional specie(s)
  Tetra-functional specie(s)
  Catalyst
  Acid Methods
1. Modestly dilute concentrated stock HCl or other strong acid (dilutions will range)
2. Rigorously dilute a separate batch of concentrated stock HCl or other strong acid (dilutions will range)
3. Add varying ratios of di-, tri-, and tetra-functional species that equal 1 mL to 10 mL DI H$_2$O
4. Add modestly dilute HCl or other strong acid to DI H$_2$O with siloxane monomers
5. Stir or mix for 18 hrs
6. Centrifuge at 2000×g for 5 min
7. Extract 7.5 mL of supernatant and add 7.5 mL of rigorously diluted HCl or other strong acid
8. Add 15 μL concentrated catalyst to supernatant-acidic water solution
9. Continue stirring or mixing for 30 min then centrifuge at 2000×g for 5 min
10. Wash particles and resuspend in a stable solution Results This protocol produces colloids of varying compressibilities with diameters on the order of 0.5-50 μm several minutes after the addition of a catalyst. Colloid size and compressibility depends on monomer ratio, monomer concentration, hydrolysis time, and catalyst strength. The colloids shown in FIGS. 8-11 were produced according to this Protocol III and specifically according to the following procedure.

Materials
  Siloxane monomers
    Tri-functional:
      Trimethoxymethylsilane (TMOMS)
      Vinyltrimethoxysilane (VTMOS)
    Di-functional:
      Dimethoxydimethylsilane (DMODMS)
      Vinylmethyldiethoxysilane (DMODMS)
  Triethylamine (TEA)
  200-proof ethanol (EtOH)
  Hydrochloric acid (37% in water, concentrated stock)

Methods
1. Prepare 10 mL of 0.1 M HCl (pH=1) by adding 83.3 μL 37% HCl to 9.917 mL DI H$_2$0
2. Prepare 7.5 mL of 3.16×10$^{-4}$ M (pH=3.5) by adding 23.7 μL 0.1 M HCl to 7.476 mL DI H$_2$O
3. Add 1 mL of TMOMS to 10 mL of H$_2$O or various volume ratios of di-, tri-, and tetra-functional species
4. Add 219.5 μL of 0.1 M HCl to DI H$_2$O with monomers to obtain net pH of 2.7
5. Stir at 500 rpm for 18 hrs
6. Centrifuge at 2000×g for 5 min
7. Extract 7.5 mL of supernatant and add 7.5 mL of 3.1×10$^{-4}$ M HCl
8. Add 15 μL TEA to supernatant-acidic water solution
9. Continue stirring for 30 min at 500 rpm
10. Centrifuge at 2000×g for 5 min
11. Resuspend pellet in 10 mL EtOH and sonicate FIGS. 8A-8D are SEM images of colloids synthesized using Protocol III at various magnifications according to one or more embodiments of the present disclosure. FMAR colloids were synthesized via rapid bulk synthesis using the siloxane monomer trimethoxymethylsilane (TMOMS). A) Particles are shown at a magnification of 5000×. B) Particles are shown are shown at a magnification of 15000×. C) Particles are shown at a magnification of 15000× at a different site than shown in (B). D) Particles are shown at a magnification of 2500×.

Figure 9:
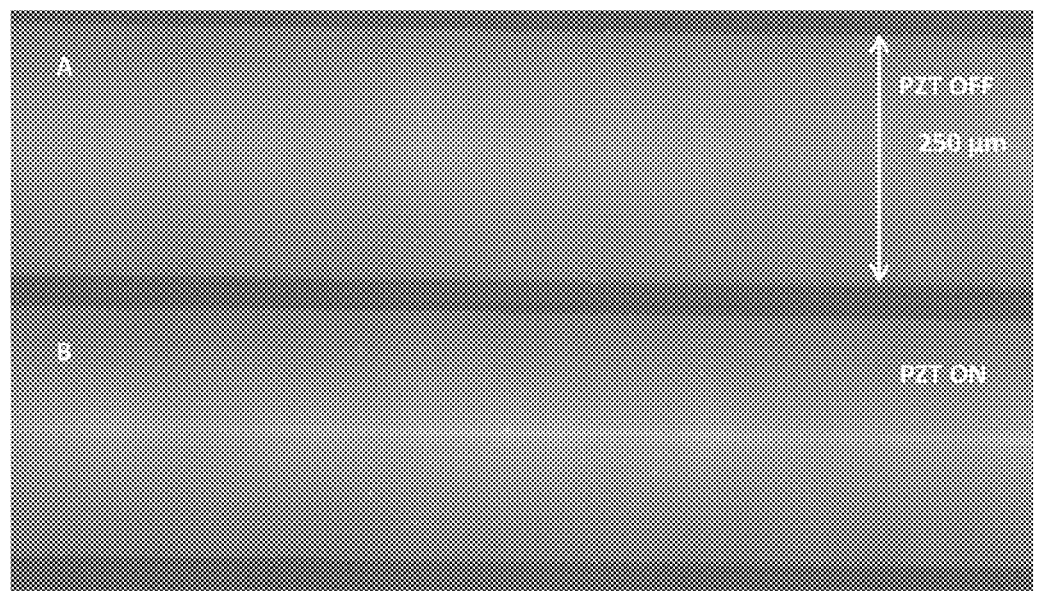
FIG. 9 shows positive acoustic contrast FMAR colloids synthesized using Protocol III as described in FIG. 8 in a silicon acoustofluidic chip as a demonstration of the acoustic tunability of the synthesis mechanisms according to one or more embodiments of the present disclosure. A) The acoustic field is turned off. B) FMAR colloids responding to the acoustic field, focusing in the center of the channel (acoustic node) indicating FMAR colloids can be easily designed to exhibit positive acoustic contrast.

FIG. 9 shows positive acoustic contrast FMAR colloids synthesized using Protocol III as described in FIG. 8 in a silicon acoustofluidic chip as a demonstration of the acoustic tunability of the synthesis mechanisms according to one or more embodiments of the present disclosure. A) The acoustic field is turned off. B) FMAR colloids responding to the acoustic field, focusing in the center of the channel (acoustic node) indicating FMAR colloids can be easily designed to exhibit positive acoustic contrast.

Figure 10:
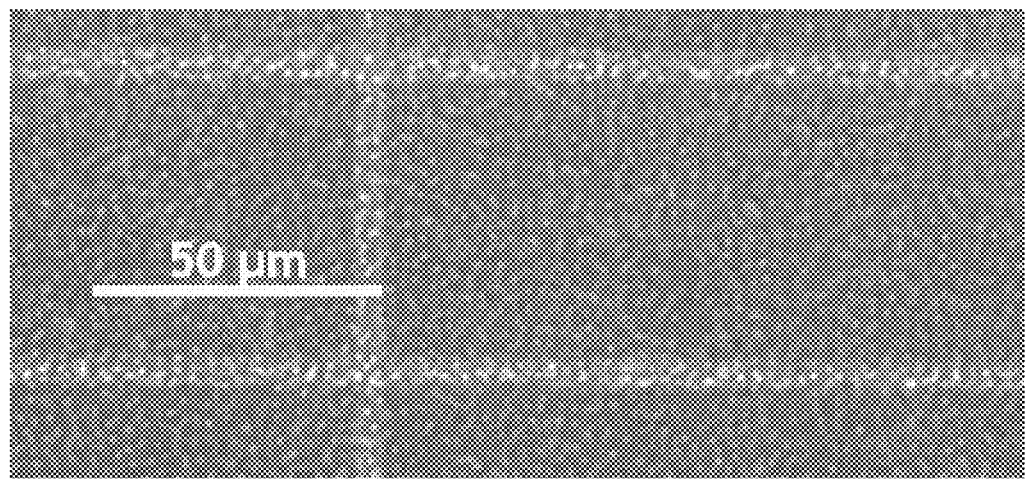
FIG. 10 is an optical micrograph of FMAR colloids synthesized using Protocol III as described in FIG. 8.

FIG. 10 is an optical micrograph of FMAR colloids synthesized using Protocol III as described in FIG. 8.

Figure 11A:
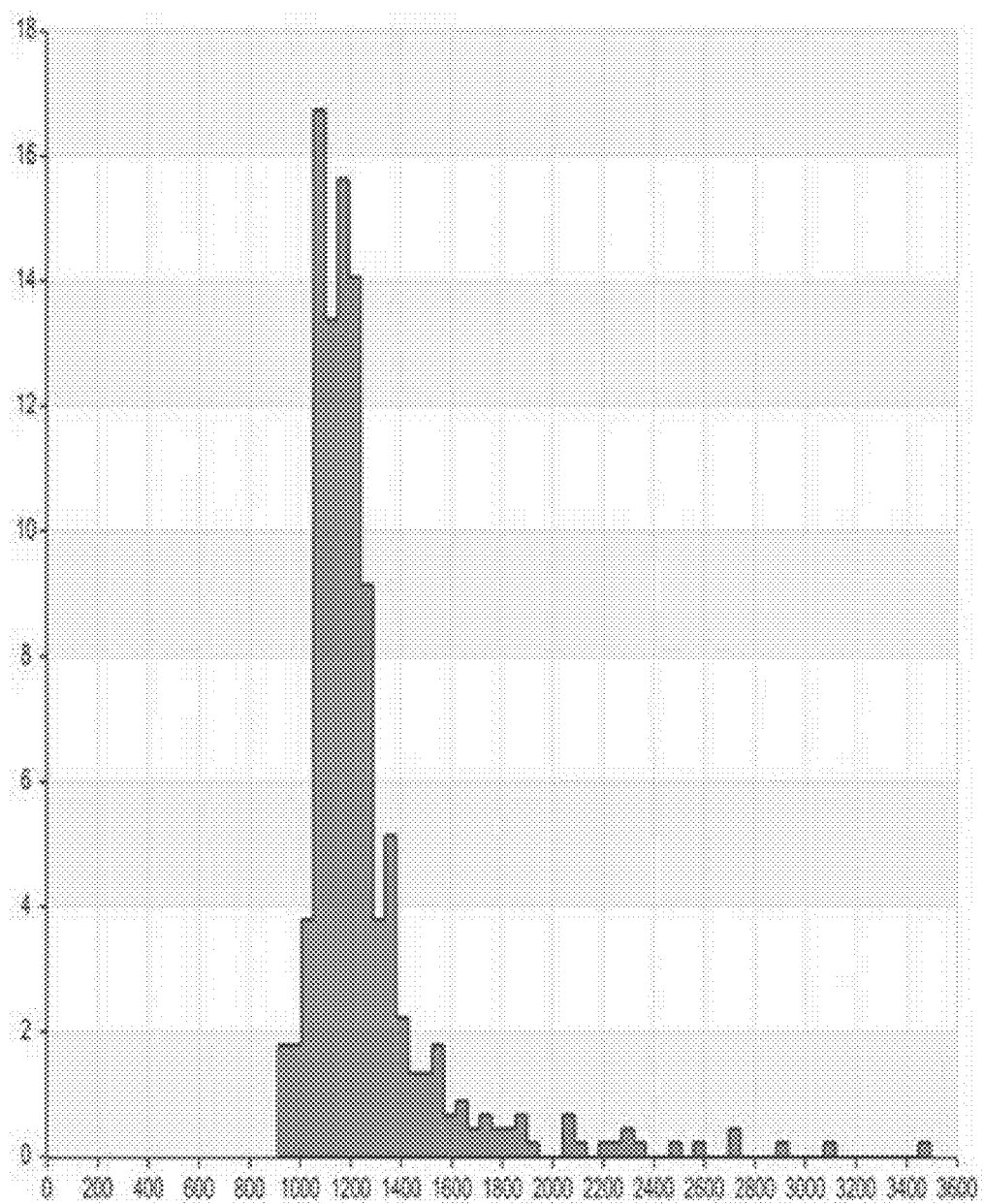
FIGS. 11A-11B are graphs showing size distribution of FMAR colloids synthesized using Protocol III as described in FIG. 8 characterized by a qNANO device according to one or more embodiments of the present disclosure. Particle diameter is shown on the x axis and percent population by count is shown on the y axis. The coefficient of variance was A) 12.39% and B) 14.01%.
Figure 11B:
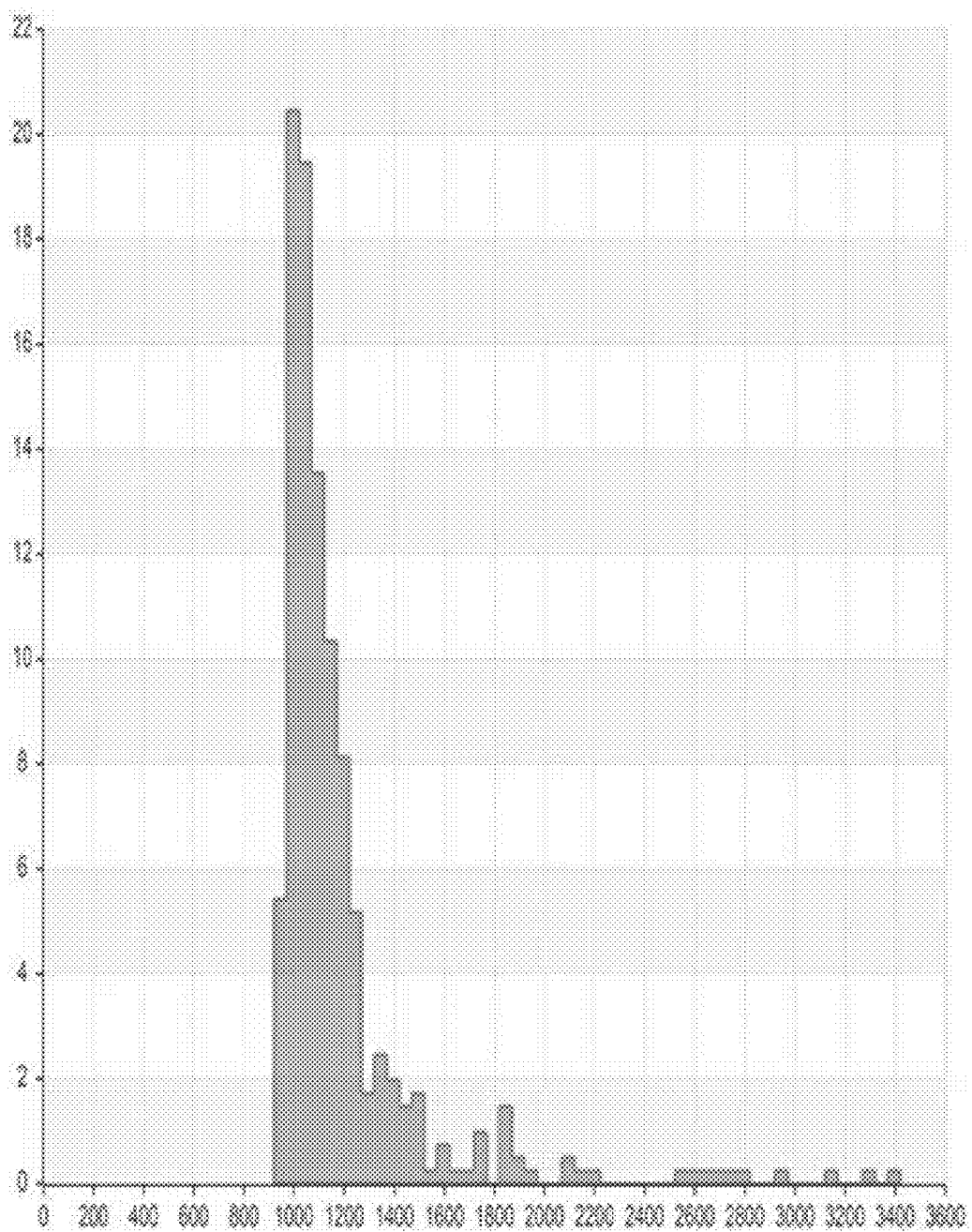

FIGS. 11A-11B are graphs showing size distribution of FMAR colloids synthesized using Protocol III as described in FIG. 8 characterized by a qNANO device according to one or more embodiments of the present disclosure. Particle diameter is shown on the x axis and percent population by count is shown on the y axis. The coefficient of variance was A) 12.39% and B) 14.01%.

Protocol IV (Core-Shell Method)
  Materials
    Di-functional specie(s)
    Tri-functional specie(s)
    Tetra-functional specie(s)
    Catalyst
    Acid
  Methods
    i. Acid Preparation
      1. Modestly dilute concentrated stock HCl or other strong acid (dilutions will range)
      2. Rigorously dilute a separate batch of concentrated stock HCl or other strong acid (dilutions will range)
    ii. Semi-Rigid Shell Hydrolysis
      1. Add 1 mL of varying ratios of tri- and tetra-functional species to 10 mL of DI $H_2O$
      2. Add 200 μL of modestly dilute HCl or other strong acid to DI $H_2O$ solution with tri-/tetra-functional monomers
      3. Vigorously stir or mix for 18 hrs
    iii. Emulsion Core Hydrolysis
      1. Add 1 mL of di-functional species to 10 mL DI $H_2O$
      2. Add 200 μL of modestly dilute HCl or other strong acid to DI $H_2O$ solution with di-functional monomers
      3. Vigorously stir or mix for 6 hrs
    iv. Emulsion Core Synthesis
      1. Centrifuge di-functional monomer-containing solution at 2000×g for 5 min
      2. Extract 7.5 mL of supernatant and add 7.5 mL of rigorously dilute HCl or other strong acid
      3. Add 30 μL concentrated catalyst to supernatant-acidic water solution
      4. Continue stirring or mixing for 30 min
    v. Semi-rigid Shell Polycondensation
      1. Centrifuge at 2000×g for 5 min
      2. Extract 7.5 mL of supernatant and add 7.5 mL of $3.1 \times 10^{-4}$ M HCl and mix
      3. Directly add the 10 mL acidic supernatant to the emulsion core solution, continue stirring
      4. Immediately add 10 μL concentrated catalyst
      5. Continue stirring or mixing for 30 min Results This protocol produces colloids of varying compressibilities with diameters on the order of 0.5-10 μm several minutes after the addition of a catalyst. Colloid size and compressibility depends on monomer ratio, monomer concentration, hydrolysis time, and catalyst strength. The colloids shown in FIGS. 12 and 13 were produced using this Protocol. Specifically, the colloids shown in FIGS. 12 and 13 were produced according to the following procedure.

Figure 12:
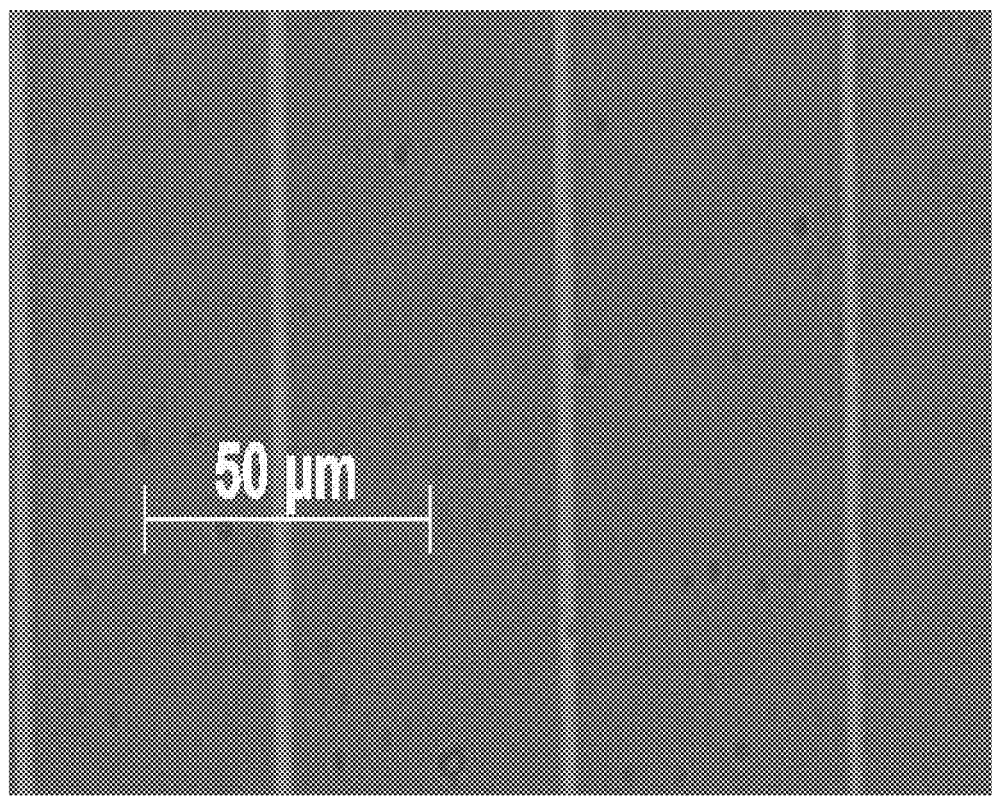
FIG. 12 is an optical micrograph of colloids synthesized using Protocol IV according to one or more embodiments of the present disclosure. The particle cores were made using dimethoxydimethylsilane (DMODMS) siloxane monomers and the particle shells were made using trimethoxymethylsilane (TMOMS).

Materials
  Siloxane Monomers
    Tri-functional:
      Trimethoxymethylsilane (TMOMS)
      Vinyltrimethoxysilane (VTMOS)
    Di-functional:
      Dimethoxydimethylsilane (DMODMS)
      Vinylmethyldiethoxysilane (DMODMS)
  Triethylamine (TEA)
  200-proof ethanol (EtOH)
  Hydrochloric acid (37% in water, concentrated stock)
Methods
  A. Acid Preparation
    10. Prepare 10 mL of 0.1 M HCl (pH=1) by adding 83.3 μL 37% HCl to 9.917 mL $H_2O$
    11. Prepare 7.5 mL of $3.16 \times 10^{-4}$ M (pH=3.5) by adding 23.7 μL of 0.1M HCl to 7.476 mL $H_2O$
  B. Semi-Rigid Shell Hydrolysis (Start at 10 pm Day 1, Finish 10:15 pm Day 1)
    4. Add 1 mL of TMOMS to 10 mL of $H_2O$ or various volume ratios of tri- and tetra-functional species
    5. Add 219.5 μL of 0.1M HCl to $H_2O$ with TMOMS to obtain net pH of 2.7
    6. Stir at 500 rpm for 18 hrs
  C. Emulsion Core Hydrolysis (Start at 9:30 am Day 2)
    1. Add 1 mL of DMODMS to 10 mL of $H_2O$
    2. Add 219.5 μL of 0.1M HCl to $H_2O$ with DMODMS to obtain net pH of 2.7
    3. Stir at 500 rpm for 6 hours
  D. Emulsion Core Synthesis (Start at 3:30 pm Day 2, Finish 4:15 pm Day 2)
    5. Centrifuge DMODMS $H_2O$ at 2000×g for 5 min
    6. Extract 7.5 mL of supernatant and add 7.5 mL of $3.1 \times 10^{-4}$ M HCl
    7. Add 30 μL TEA to supernatant-acidic water solution
    8. Continue stirring for 30 min at 500 rpm
    9. Dispose 5 mL of the solution
  E. Semi-Rigid Shell Polycondensation (Start at ~4:00 pm Day 2, Finish 4:15 pm Day 2)
    1. Centrifuge at 2000×g for 5 min
    2. Extract 7.5 mL of supernatant and add 7.5 mL of $3.1 \times 10^{-4}$ M HCl and mix
    3. Directly add the 10 mL acidic supernatant to the emulsion core solution, continue stirring
    4. Immediately add 10 μL TEA
    5. Continue stirring for 30 min at 500 rpm FIG. 12 is an optical micrograph of colloids synthesized using Protocol IV according to one or more embodiments of the present disclosure. The particle cores were made using dimethoxydimethylsilane (DMODMS) siloxane monomers and the particle shells were made using trimethoxymethylsilane (TMOMS).

Figure 13:
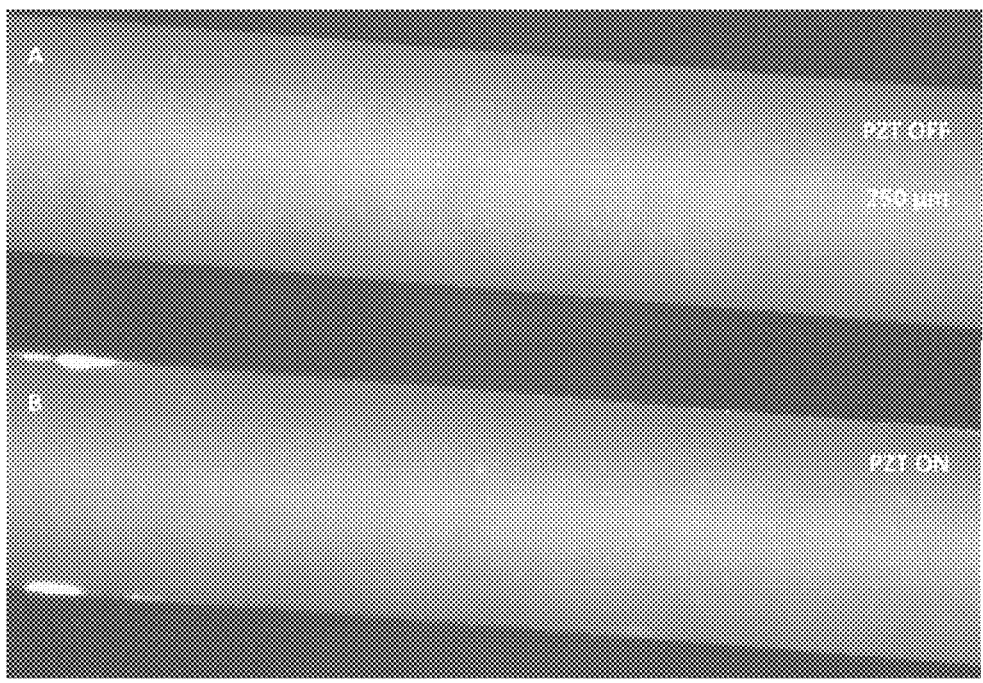
FIG. 13 is an image of a silicon acoustofluidic channel containing FMAR colloids synthesized from Protocol IV as described in FIG. 12 according to one or more embodiments of the present disclosure. A) (PZT Off), Flow=100 uL/min. B) (PZT On, V=10), Flow=turned off for 60 sec.

FIG. 13 is an image of a silicon acoustofluidic channel containing FMAR colloids synthesized from Protocol IV as described in FIG. 12 according to one or more embodiments of the present disclosure. A) (PZT Off), Flow=100 uL/min. B) (PZT On, V=10), Flow=turned off for 60 sec.

Example 2

Figure 14:
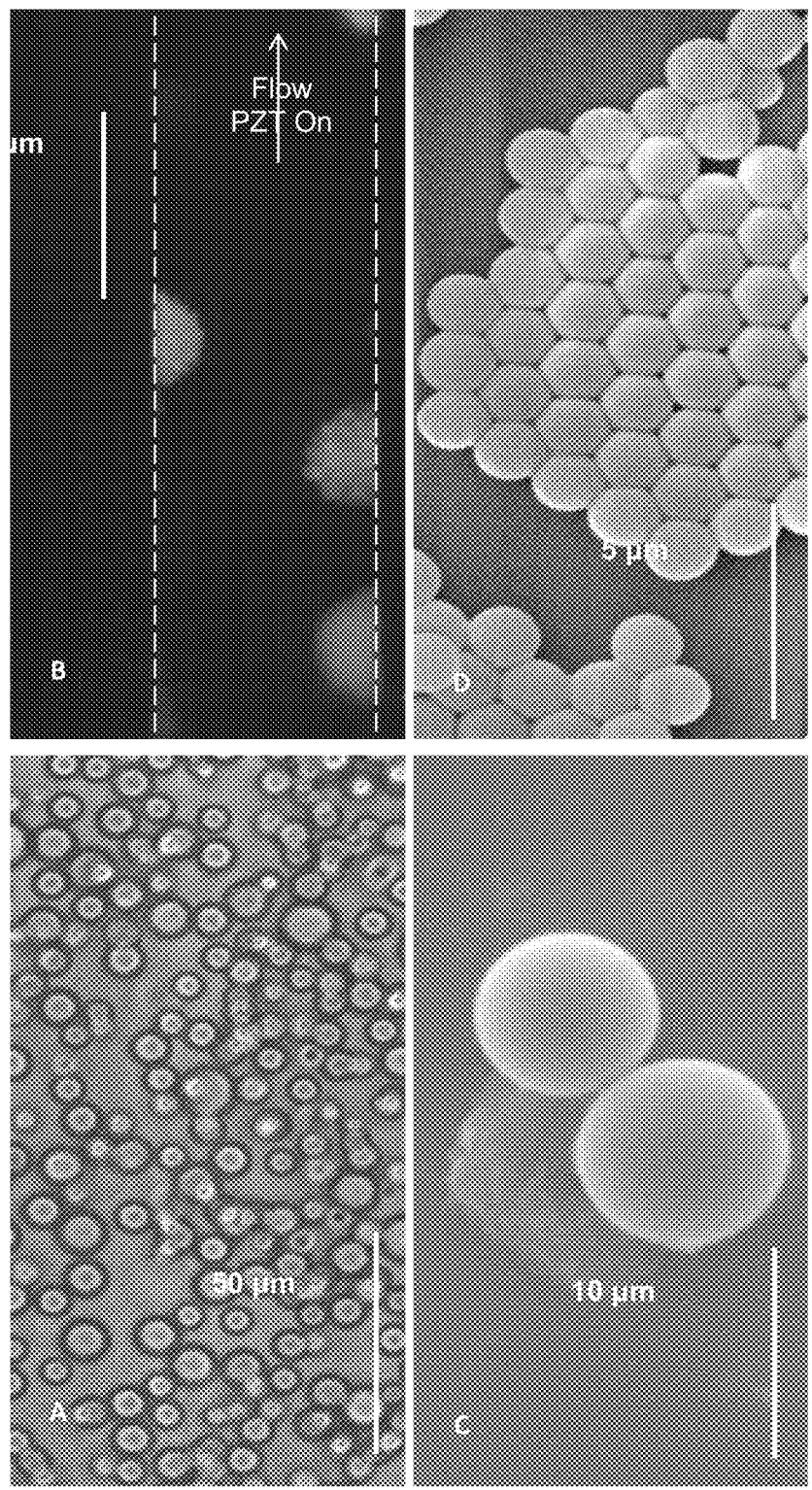
FIGS. 14A-14D are images of FMAR colloids made according to one or more embodiments of the present disclosure. A) Optical micrograph of elastomeric FMAR colloids for cell separation made according to Protocol II using the siloxane monomers trimethoxymethylsilane (TMOS) and the siloxane monomers dimethoxydimethylsilane (DMODMS) at a ratio of 1:100. B) Fluorescence micrograph of the elastomeric FMAR colloids made according to Protocol II using functional monomers TMOS and DMODMS at a ratio of 1:100 with adsorbed Nile red. C) SEM image of biotin polystyrene (SPHEROTECH, INC.) bound to a KG-1a human myeloblast cell. D) SEM of highly monodisperse FMAR colloids made according to Protocol III using only functional TMOMS monomers.
Figure 15:
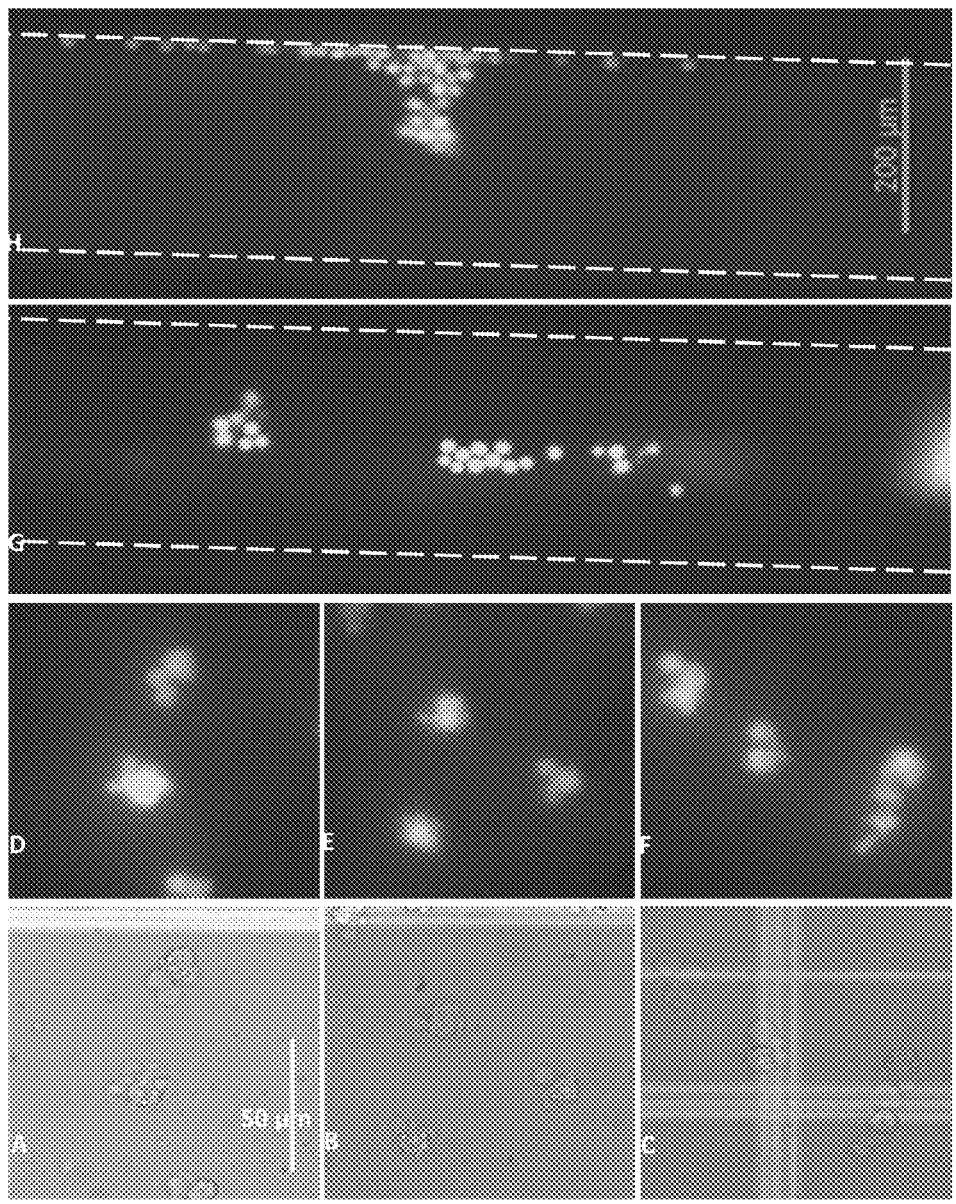
FIGS. 15A-15H are images of KG-1a cell binding and separation according to one or more embodiments of the present disclosure. A-C) Optical micrographs of streptavidin adsorbed elastomeric FMAR colloids (1:100 TMOS: DMODMS as described in FIGS. 14A&B) binding to Calcein AM dyed KG-1a cells. D-F) Fluorescence microscopy images of Calcein AM dyed KG-1a cells illuminating the bound non-fluorescent FMAR colloids, demonstrating binding (same frames as FIG. 3A-C). G) Unbound KG-1a cells focusing in the acoustic node of a silicon acoustofluidic channel. H) KG-1a cells bound to the elastomeric FMAR colloids focusing to the acoustic antinode of the silicon acoustofluidic channel. Note: The scale bar in A is also for B-F and the scale bar in H is also for G.
Figure 16:
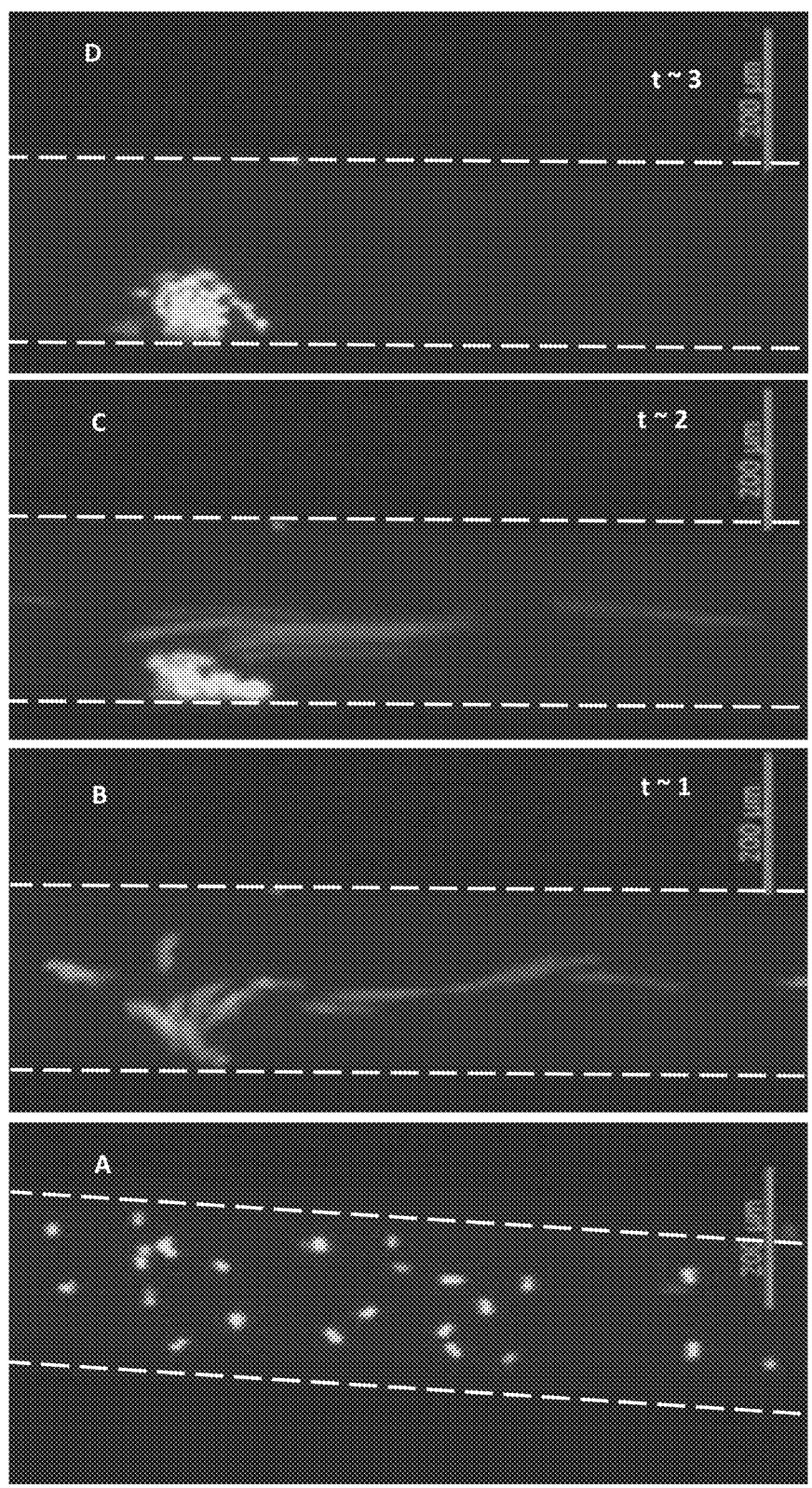
FIGS. 16A-D are images of the use of FMAR colloids in silicon acoustofluidic channels to effect acoustophoretic cell displacement according to one or more embodiments of the present disclosure. KG-1a cells spontaneously migrate to the pressure antinode in the presence of an acoustic standing wave when bound to FMAR colloids as described in FIGS. 14A & 14B. A) Shows a representative random distribution of fluorescent cells in an acoustofluidic device without a standing wave. B-D) Show cells responding to the primary radiation force (time step is approximately 1 sec).

Use of FMAR Colloids in Silicon Acoustofluidic Channels to Effect Acoustophoretic Cell Displacement The following examples show the utility of using the FMAR colloids synthesized according to the Protocols described above to separate cells in a silicon acoustofluidic chip. FIG. 14 shows images of FMAR colloids made according to one or more embodiments of the present disclosure. In FIG. 14A, an optical micrograph is shown of elastomeric FMAR colloids for cell separation made according to Protocol II using tetra-functional functional monomers trimethoxymethylsilane (TMOS) and di-functional dimethoxydimethylsilane (DMODMS) at a ratio of 1:100. FIG. 14B shows a fluorescence micrograph of the elastomeric FMAR colloids with adsorbed Nile red in a silicon acoustofluidic chip. When the acoustic field is turned on, the FMAR colloids respond to the acoustic field by focusing in at the acoustic antinodes indicating FMAR colloids can be easily designed to exhibit negative acoustic contrast. FIG. 14C shows an SEM image of biotin polystyrene (SPHEROTECH, INC.) bound to a KG-1a human myeloblast.

FIGS. 15A-15H are images of KG-1a cell binding and separation according to one or more embodiments of the present disclosure. A-C) Optical micrographs of streptavidin adsorbed elastomeric FMAR colloids (1:100 TMOS: DMODMS as described in FIGS. 14A&B) binding to Calcein AM dyed KG-1a cells. D-F) Fluorescence microscopy images of Calcein AM dyed KG-1a cells illuminating the bound non-fluorescent FMAR colloids, demonstrating binding (same frames as FIG. 3A-C). G) Unbound KG-1a cells focusing in the acoustic node of a silicon acoustofluidic channel. H) KG-1a cells bound to the elastomeric FMAR colloids focusing to the acoustic antinode of the silicon acoustofluidic channel. Note: The scale bar in A is also for B-F and the scale bar in H is also for G.

FIGS. 16A-D are images of the use of FMAR colloids in silicon acoustofluidic channels to effect acoustophoretic cell displacement according to one or more embodiments of the present disclosure. KG-1a cells spontaneously migrate to the pressure antinode in the presence of an acoustic standing wave when bound to FMAR colloids as described in FIGS. 14A & 14B. A) Shows a representative random distribution of fluorescent cells in an acoustofluidic device without a standing wave. B-D) Show cells responding to the primary radiation force (time step is approximately 1 sec).

Example 3

Preparation & Characterization of Negative Acoustic Contrast Particles (NACPs) Having a Functional Group Available for Covalent Modification Preparation of stable, biofunctionalized elastomeric particles (NACPs): An important goal is to be able to employ NACPs for bioanalytical techniques that require biofunctionalization of the particle surface for binding to specific biomolecules or cells. Common bioconjugation schemes, such as carboiimide chemical approaches, are not feasible with NACPs synthesized using the common silicone material (e.g., polydimethylsiloxane "PDMS"), because the resulting PDMS NACPs lack the necessary functional groups such as carboxylates, hydroxyls, epoxies, and amines to introduce functionality. To address this problem, polyvinylmethylsiloxane (PVMS) pre-polymers were used to generate NACPs with surface vinyl groups that would be useful for reactions such thiolene. In this manner, a variety of chemical reactions could be employed to functionalize the vinyl containing NACPs. For example, thiolene click reactions using biotinylated thiols and a water soluble azothermal initiator (VA-50, WAKO) or photoactivated biotin-benzophenone could be employed to covalently biofunctionalize the vinyl-containing NACPs.

Below is an example of a protocol that was used to prepare such biofunctional NACPs with PVMS. A mixture of 1.02 g of hydroxyl-terminated PVMS, 0.07 g vinylmethoxysiloxane homopolymer (GELEST), were thoroughly stirred and combined with a solution of 0.1 gram PLURONIC F108 (ALDRICH) in 15 mL of MILLIQ water, briefly vortexed, and homogenized using a POLYTRON PT 1200E homogenizer for 5 min at 6500 rpm. After stirring at 50° C. for 4 hrs, the polydisperse emulsion was permitted to cure at ambient conditions for at least 7 days before being passed through a 12 μm polycarbonate filter (WHATMAN) and stored at ambient conditions until use. Biotinylation of PVMS microparticles occurred by first washing $7.2 \times 10^7$ microparticles with 1×PBS by centrifuging at 8000×g, 2 min and resuspending the pellet with a final volume of 2 mL of 1×PBS. The microparticles were transferred to a glass vial with a stir bar and 3.3 mg Biotin-PEG-tetrofluorophenyl azide (Biotin-PEG-TFPA, QUANTA BIODESIGN) in 100 μL of dimethylacetamide (DMAC) was added. The Biotin-PEG-TFPA is a photoaffinity molecule that reacts with a variety of groups (e.g., C—H bonds) via nitrene formation. A light source (OMINICURE) with light guide was placed 500 mm above the stirring solution for 30 minutes at a light intensity of 100 mW/cm$^2$ at 365 nm as measured by a power meter. The resultant slightly yellow solution was stored at 4° C. until use. The biotinylation of the EP surfaces in this manner permits linking of commercially available biotinylated antibodies and other molecules via streptavidin protein. The NACPs synthesized as described above using biotinylated tetrafluorophenyl azide (Biotin-PEG-TFPA) proved successful for biofunctionalization. For example, the NACPs modified with Biotin-PEG-TFPA remained stable, dispersed, and able to bind Streptavidin (data not shown).

Figure 17:
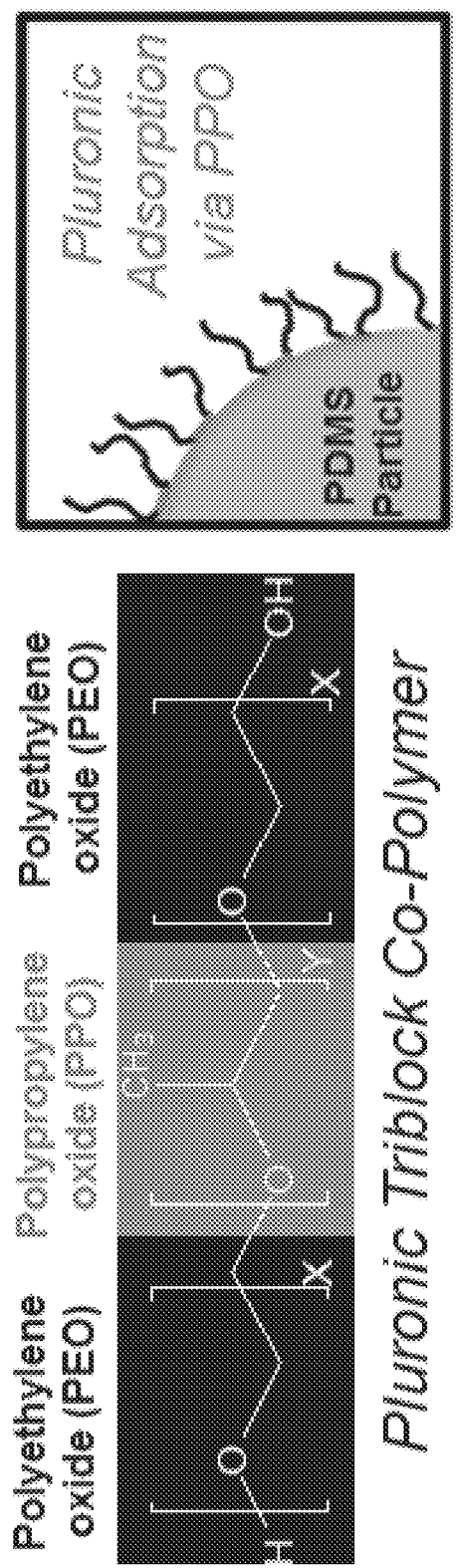
FIGS. 17A-17B are schematic diagrams showing the chemical structure of a triblock co-polymer surfactant A) and the surfactant associated with a NACP B) according to one or more embodiments of the present disclosure.

In another experiment, surfactant PLURONIC F108 (ALDRICH) was functionalized with the Biotin-PEG-TFPA described above, and then the biotinylated surfactant was used during the synthesis of the NACPs as described above using PVMS NACPs. FIGS. 17A and B are schematic diagrams showing the chemical structure of the F108 triblock co-polymer surfactant and the surfactant associated with an NACP, respectively. The resulting compressible, surfactant biofunctionalized PVMS NACPs were used in an experiment in an acoustic channel with incompressible cells without a label that had been stained with calein AM for imaging purposes. The purpose of this experiment was to show that PVMS NACPs and cells (when not bound) respond differently to an ultrasonic standing wave. The results showed that the surfactant biofunctionalized NACPs segregated to the periphery of the acoustic channel under an applied frequency of 2.93 MHz while at the same time, the incompressible cells stained with calein AM located to the central axis of the microfluidic channel (data not shown).

Figure 18:
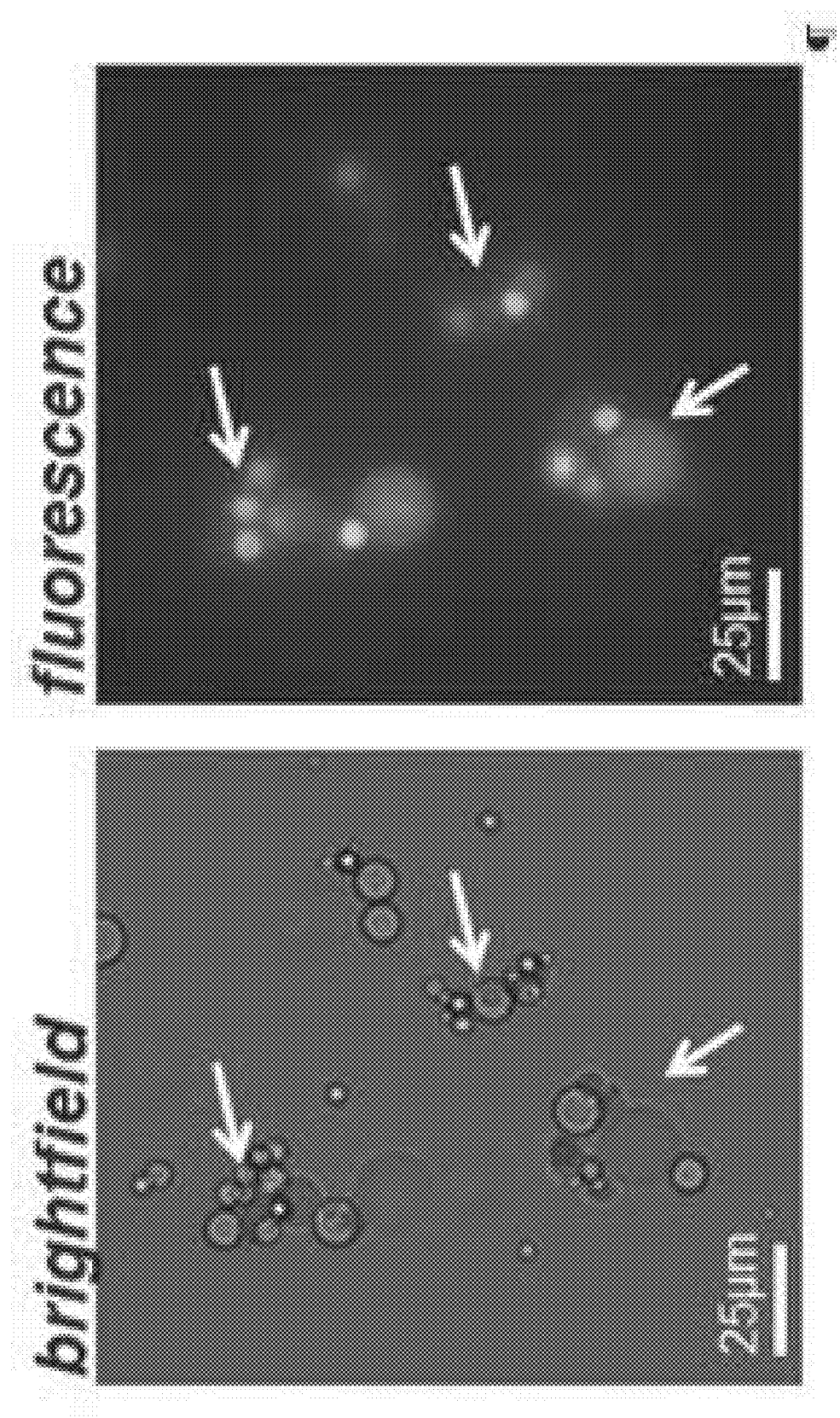
FIG. 18 shows brightfield (left panel) and fluorescent microscope (right panel) images of binding between surfactant biotin functionalized PDMS NACPs (large circles) and streptavidin-functionalized polystyrene beads (smaller circles) according to one or more embodiments of the present disclosure.

In a related experiment, PDMS NACPs were prepared with biotinylated-F108. The surfactant biotin functionalized NACPs were incubated with microparticles functionalized with Streptavidin (Polysciences, Green microparticles, 6 µm diameter) for 30 min and washed and imaged. The streptavidin with its four biotin binding sites serves as a linker between the biotinylated NACPs and the streptavidin-functionalized particles. FIG. 18 shows brightfield (left panel) and accompanying fluorescent microscope (right panel) images of binding between NACPs functionalized with biotin-surfactant (large circles) and the streptavidin-functionalized polystyrene beads (smaller circles).

A CD34+ cell line (Kg-1a) was employed as a model system to investigate acoustic-mediated cell separation using bio functionalized NACPs. Separation, collection, and analysis of CD34+ cells is significant for reasons including repopulation of marrow for autologous stem cell transplantation and characterization of malignancies such as acute lymphoblastic leukemia. CD34+ cells were pre-functionalized with biotinylated monoclonal antibodies (CD34, mouse anti-human) and fluorescent ALEXAFLUOR-488 streptavidin before incubation with the biotinylated PVMS NACPs described above. The streptavidin with its four biotin binding sites serves as a linker between the biotinylated NACPs and the streptavidin-labeled cells. Some binding between cells and particles was observed (data not shown). Next, the EP-cell complexes were introduced into the aforementioned acoustic chip with an applied frequency of 2.93 MHz. Observation using fluorescent microscopy through the glass lid of the acoustic chip showed migration of the NACP-bound CD34+ cells from the acoustic node to the periphery (antinodes) of the acoustic channel (data not shown).

In another example, biofunctionalized PVMS NACPs were prepared according to the following procedure. A mixture of 1.0 g of hydroxyl-terminated PVMS,[14] 0.07 g vinylmethoxysiloxane homopolymer (GELEST), and 0.02 g tin octoate catalyst (GELEST) was thoroughly stirred and combined with a solution of 0.5 or 0.7 wt % PLURONIC F108 (ALDRICH) in ultrapure water (Mill-Q, 18MΩ resistivity). The mixture was briefly vortexed, homogenized using a PT 1200E homogenizer (POLYTRON) with a 3 mm rotor for 5 min at 18.750 rpm, and stirred for at least 2 hrs at 50° C. The polydisperse emulsion was permitted to cure via alkoxy condensation of silanol-terminated PVMS with vinylmethoxysiloxane. Particles were filtered through a 12 µm polycarbonate membrane (WHATMAN, CYCLOPORE) and stored at ambient conditions until use.

Preparing PDMS particles: A mixture comprising a 1:10 weight ratio of curing agent:base of SYLGARD 184 (DOW CHEMICAL) was thoroughly mixed and subsequently combined with 1 wt % of F108. The mixture was homogenized as previously described. The emulsion was incubated at 45° C., stirring for at least 1.5 hrs and subsequently left at ambient conditions for at least 12 hrs to permit curing.

Functionalization: For reactions biotin-PEG-TFPA, ~5×10⁷ PVMS microparticles were washed with 1×PBS by centrifuging and resuspending the pellet in a final volume of 2 mL of 1×PBS. The microparticles were transferred to a cylindrical glass vial (2.5 cm diameter) and 3 mg biotin-PEG-TFPA in 100 µL of dimethylacetamide was added. Light irradiation occurred using an OMNICURE S1000 equipped with a high pressure mercury lamp and an internal 320-500 nm filter. The associated light guide was placed ~5 mm above the stirring solution for 30 min at a light intensity of ~100 mW/cm² at a wavelength of 365 nm, (as measured by POWERMAX USB SENSOR, COHERENT). The resultant yellow solution was stored at 4-C until use. Biotinylation of F108 surfactant followed a similarly reported protocol.[18] Briefly, hydroxyl end groups on F108 were modified to succinimidyl carbonate using N,N'-disuccinimidyl carbonate (ALDRICH) and 4-(dimethylamino)pyridine (Aldrich) and subsequently reacted with biotin-hydrazide (ALDRICH). Once biotinylated. F108 was used to prepare silicone emulsions as previously described. Subsequent addition of streptavidin (ALEXAFLUOR 4880R ALEXAFLUOR 546) to NACPs occurred by washing particles at least three times by centrifuging and resuspending the pellet in 1×PBS, and incubating with either 1 µM or 1.7 µM of streptavidin for 30 min at room temperature.

Characterization of negative acoustic contrast materials and microparticles. Attenuated total reflection-Fourier transform infrared (ATR-FTIR) spectra were acquired using a THERMO ELECTRON NICOLET 8700 spectrometer (Ge crystal, 32 scans, 4 cm² resolution). Scanning electron microscopy (SEM) images were obtained using model FEI XL 30 SEM under ultra-high resolution mode after sputter coating the samples with approximately 6 nm of gold. Optical microscopy images were obtained using an upright ZEISS AXIO IMAGER A2 microscope with appropriate filter set (ex 470/40, em 525/50 or ex 545/25, em 605/70 or ex 395, em445/50).

Bioseparation studies. Binding between streptavidin polystyrene microparticles (POLYSCIENCES, YG microspheres, 6 µm) and PDMS NACPs (encapsulated with rhodamine B, functionalized with biotin-F108) occurred by combining ~10⁶ polystyrene particles and ~10⁷ PDMS particles and incubating with end-over-end rotation for 30 min at room temperature. PDMS NACPs were washed three times with 1×PBS before combining with the polystyrene microparticles. Polystyrene particles were added directly from the manufacture's stock without washing. Bioseparation events within a channel were monitored through the glass lid of the acoustofluidic device prepared as described in Example 1 using fluorescent microscopy.

Results: Silicone elastomers offer properties suitable for NACPs such as compressibility at mild temperature (e.g., Young's modulus ~1 MPa for typical PDMS formulations).[12] Here, all NACPs were prepared by emulsifying silicone pre-polymers in aqueous surfactant solutions and subsequently curing to produce solid microparticles. Because homogenization produces polydisperse particles, filtration or centrifugation was employed to narrow the breadth of particle size distributions. In one example, filtration of NACPs with a 12 µm polycarbonate filter resulted in an average particle diameter of 6±3 µm (data not shown). Although a variety of surfactants enabled formation of silicone-in-water emulsions, the importance of surfactant type became evident when attempting to re-suspend cured NACPs in surfactant-free buffer, which often resulted in irreversible particle aggregation. Here, it was found that the block copolymer surfactant, F108, stabilizes silicone microparticles likely due to the strong association of the hydrophobic polypropylene oxide block with silicone.[13] This stable association was further exploited by end-functionalizing F108 with biotin (see FIGS. 17 and 18). Biotin-functionalized F108 enables use of the streptavidin protein as a linker between NACPs and any biotinylated analyte (e.g., cells labelled with biotinylated antibodies).

The feasibility of direct modification of NACPs was also evaluated. Typically, surface modification of PDMS is accomplished by employing modification methods such as ultraviolet (UV)/ozone irradiation,[14] UV graft polymerization,[11] oxygen plasma treatment,[15] and adsorption.[16] These modification approaches are usually performed on macroscopic silicone surfaces not held to the unique stringencies required to functionalize NACPS. For the NACPs described herein, conditions were avoided that resulted in significant change in modulus or irreversible microparticle aggregation. For instance, modification of PDMS surfaces via oxygen plasma results in the formation of brittle silica layers[17] which could affect the negative acoustic contrast property. Here, to evaluate direct, covalent modification of particles, we used PVMS which contains vinyl groups and can be functionalized chemically without forming a silica-like crust.[14]

To first evaluate and compare chemical groups in both PDMS and PVMS, bulk samples were prepared and characterized using ATR-FTIR (data not shown). PVMS material displays characteristic vinyl peaks at ~960 cm$^{-1}$ (C=C twist, =CH$_2$ wagging), ~1,410 cm$^{-1}$ (=CH$_2$ scissors), and ~1,590 cm$^{-1}$ (C=C stretch). While vinyl groups are versatile for various chemical reactions (e.g., thiolene or methathesis coupling), studies described herein revealed that relatively simple photochemical reaction with biotin-PEG-TFPA results in biofunctionalization of PVMS particles. Photoreacting biotin-PEG-TFPA with PVMS microparticles and subsequently adding fluorescent streptavidin resulted in significant differences in fluorescent signal between positive and negative samples (data not shown). For example, signal to background values (SIB) of fluorescent images of PVMS microparticles functionalized with biotin-PEG-TFPA and fluorescent streptavidin was 22±2, whereas the negative control reaction without light irradiation was 9.0±0.3, suggesting a biotinylation reaction of NACPs occurred. These studies demonstrate the utility of using biotin-PEG-TFPA for bio-functionalization of silicone microparticles.

Figure 19:
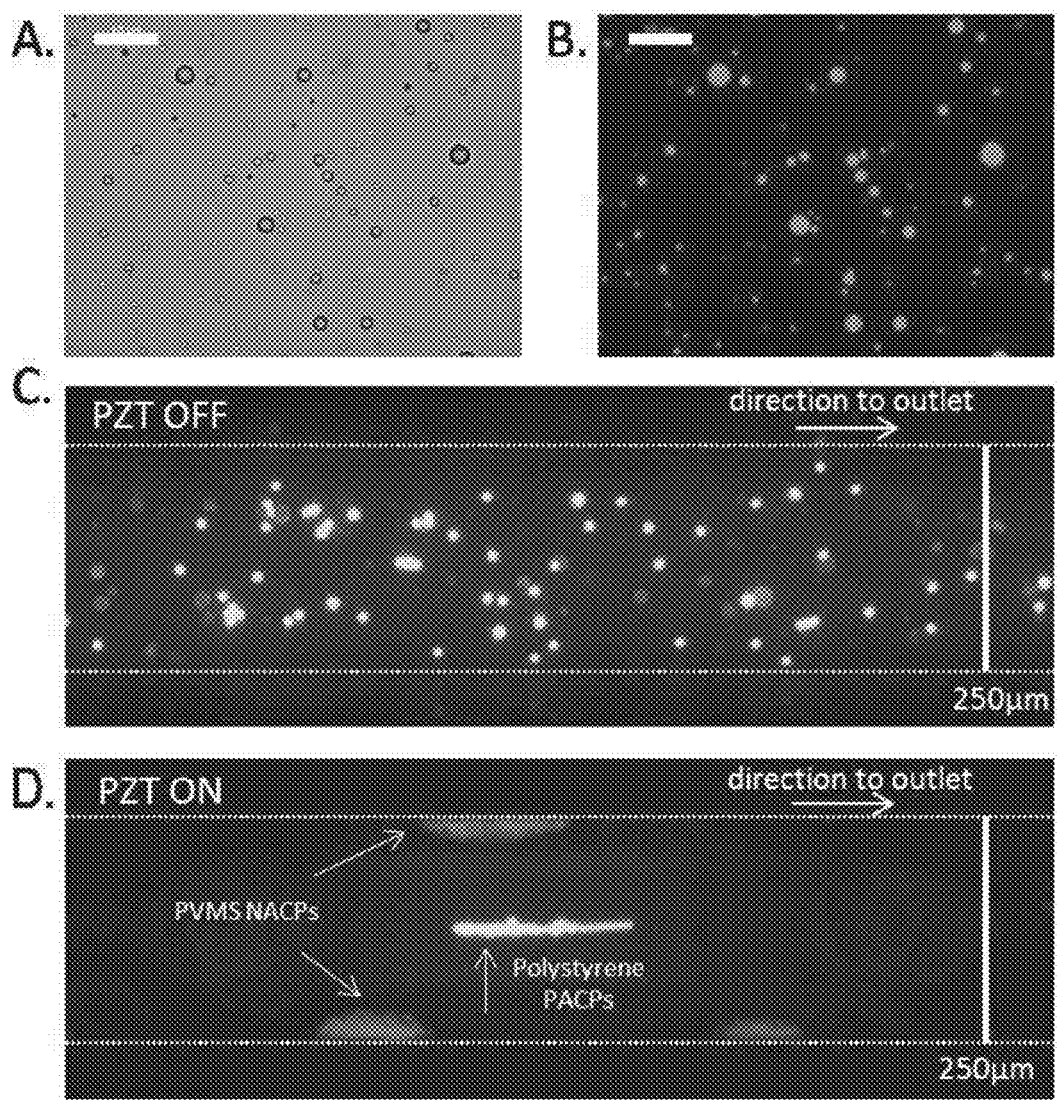
FIGS. 19A-19D show acoustic response of PVMS NACPs having a biotinlyated group covalently attached through the vinyl group of the PVMS according to one or more embodiments of the present disclosure. Brightfield image A) and corresponding fluorescence image B) of PVMS microparticles (NACPs) functionalized with biotin-PEG-TFPA and subsequently labelled with a fluorescent streptavidin. The fluorescent image was acquired during a 250 ms exposure. The scale bars represent 50 µm. C, D) Fluorescence images show a mixture of fluorescent streptavidin-functionalized NACPs (large diffuse circles, "PVMS NACPs") and non-biotinylated polystyrene beads (small bright circles, "polystyrene PACPs") within a channel of an acoustofluidic C) without and D) with activation of the PZT. Mixture contained a polystyrene:NACP ratio of 1:7. Upon generation of an ultrasound standing wave within the microchannel D), the incompressible polystyrene PACPs transport to the center of channel, corresponding to the pressure node, whereas compressible PVMS NACPs transport to the channel sidewalls, corresponding to the pressure antinodes. Images acquired in the absence of flow. Dashed lines are included to demarcate the channel boundaries.

The acoustic responsiveness of these PVMS silicone microparticles was evaluated and the images are shown in FIG. 19A-19D. The results described herein show that microparticles prepared from PVMS function as NACPs within aqueous media (see FIGS. 19A-D). For example, a mixture of biotinylated PVMS NACPs and non-biotinylated polystyrene microparticles randomly distribute within an acoustofluidic channel in the absence of a standing wave field (FIG. 19C). Upon application of an operating frequency of 2.98 MHz to generate an ultrasound standing wave within the microchannel (wavelength=2×channel width), polystyrene and PVMS microparticles rapidly separate (FIG. 19D). Incompressible positive acoustic contrast polystyrene particles transport to the center of channel, corresponding to the pressure node, whereas compressible PVMS NACPs transport to the channel sidewalls, corresponding to the pressure antinodes. The capacity for PVMS to function as NACPs (see FIGS. 19A-D) illustrates the versatility of using silicone elastomers with different chemical compositions.

Figure 20:
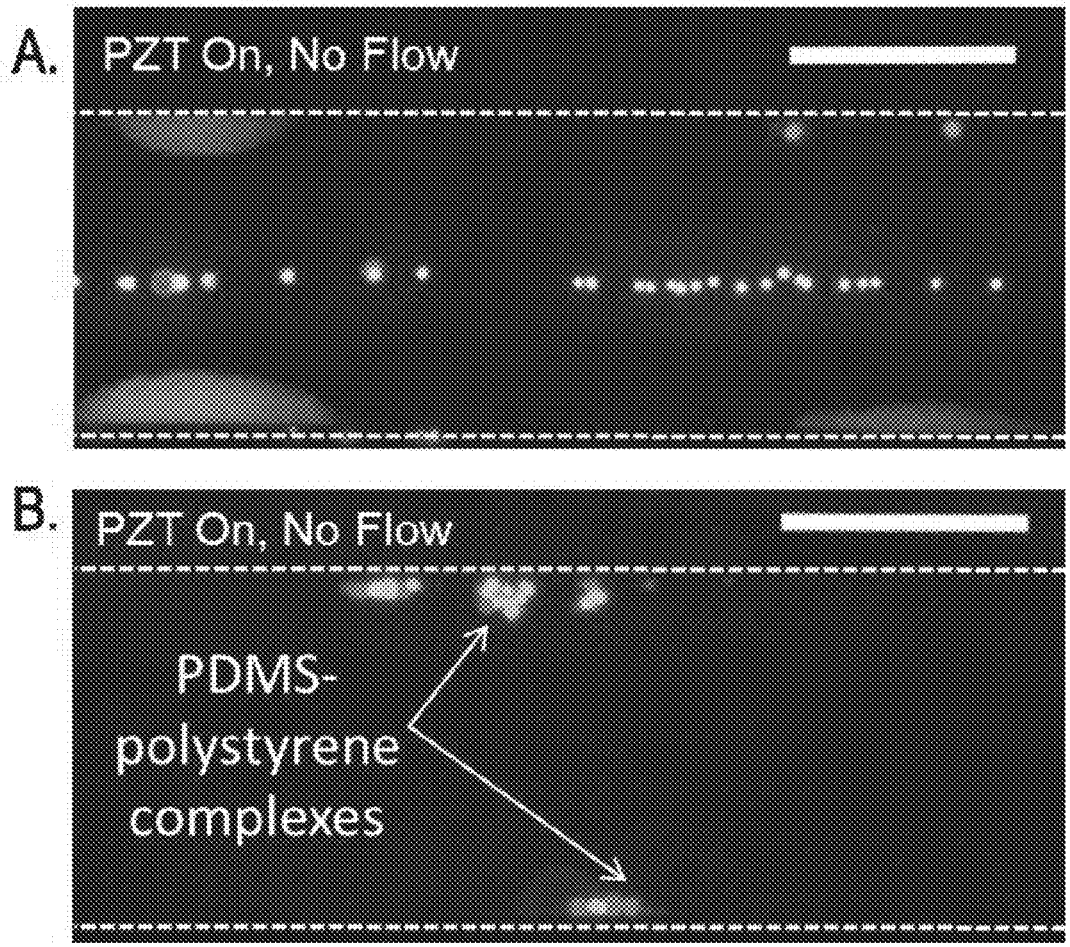
FIGS. 20A-20B are fluorescence images demonstrating the ability to use surfactant functionalized NACPs to transport positive acoustic contrast particles (PACPs) to the acoustic antinode within an acoustofluidic device according to one or more embodiments of the present disclosure. The PDMS NACPs functionalized with biotin-PLURONIC F108 transported positive acoustic contrast particles (PACPs) having a streptavidin label to the acoustic antinode. A) As a negative control, non-biotinylated PDMS NACPs encapsulated with Nile Red fluorophore (large circles) were mixed with streptavidin polystyrene microparticles PACPs (smaller and brighter circles). The lack of binding between the non-biotinylated PDMS and streptavidin polystyrene particles results in their transport to the antinode and node, respectively, in the presence of an ultrasound standing wave. B) The high affinity between the biotinylated PDMS NACPs and the streptavidin functionalized polystyrene PACPs generate particle complexes that transport collectively to the acoustic antinode within the ultrasound standing wave. Images acquired in the absence of flow with a 1:10 ratio of PACPs:NACPs. Dashed lines are included to demarcate the channel boundaries. Scale bars represent 200 µm.

The utility of the NACPs having a group that can be modified covalently with a specific biomolecular recognition group was investigated in cell separations. To this end, polystyrene microparticles were employed as surrogates for mammalian cells (i.e. as NACPs) and the separation characteristics using NACPs prepared from PDMS and a functionalized surfactant were investigated in an acoustofluidic device. As described previously and shown in the brightfield (left panel) and fluorescent (right panel) images of FIG. 18, streptavidin coated polystyrene and PDMS microparticles functionalized with biotin-PLURONIC F108 do associate when they are added together in solution. FIG. 20 shows that the NACP-polystyrene microparticle complexes (PDMS: polystyrene complexes), when placed within the acoustic-fluidic device in the presence of an acoustic wave, transport in unison to the acoustic antinode (FIG. 20B). This shows that NACPs can serve as vehicles for specific transport of positive acoustic contrast particles. Conversely, non-biotinylated PDMS microparticles did not bind the streptavidin polystyrene particles (see FIG. 20A where the non-biotinylated PDMS particles (large diffuse circles) transported to the acoustic antinode and the polystyrene microparticles (small bright circles) aligned at the acoustic node. Thus, in the absence of fluid flow NACPs accumulate at the acoustofluidic channel walls (acoustic antinode) during PZT activation (see FIGS. 19 and 20). By permitting laminar flow within the channel. NACPs will maintain their position at the acoustic antinode while simultaneously moving in a streamline flow to the downstream trifurcation, as recently demonstrated.[10] This capacity to couple relocation with downstream sample collection facilitates continuous sorting applications.

REFERENCES

All publications, patent applications, patents, and other references mentioned in the specification are indicative of the level of those skilled in the art to which the presently disclosed subject matter pertains. All publications, patent applications, patents, and other references are herein incorporated by reference to the same extent as if each individual publication, patent application, patent, and other reference was specifically and individually indicated to be incorporated by reference. It will be understood that, although a number of patent applications, patents, and other references are referred to herein, such reference does not constitute an admission that any of these documents forms part of the common general knowledge in the art.

1. Laurell T, Petersson F, Nilsson A: Chip integrated strategies for acoustic separation and manipulation of cells and particles. *Chem Soc Rev* 2007, 36: 492-506.
2. Lenshof A, Magnusson C, Laurell, T: Acoustofluidics 8: applications of acoustophoresis in continuous flow microsystems. *Lab Chip* 2012, 12:1210-1223.
3. Ward M. Turner P, DeJohn M, Kaduchak G: Unit 1.22 Fundamentals of acoustic cytometry. *Current Protocols in Cytometry* 2009, 49: 1.22.1-1.22.12.
4. Piyasena M E, Austin Suthanthiraraj P P, Applegate R W Jr., Goumas A M, Woods T A, López G P, Graves S W: Multinode acoustic focusing for parallel flow cytometry. *Anal Chem* 2012, 84:1831-1839.
5. Petersson F, Nilsson A, Holm C, Jönsson H, Laurell T: Separation of lipids from blood utilizing ultrasonic standing waves in microfluidic channels. *Analyst* 2004, 129: 938-943.
6. Petersson F, Nilsson A, Holm C, Jönsson H, Laurell T: Continuous separation of lipid particles from erythrocytes by means of laminar flow and acoustic standing waves. *Lab Chip* 2005, 5:20-22.
7. Petersson F, Åberg L, Swärd-Nilsson A M, Laurell T: Free flow acoustophoresis: microfluidic-based mode of particle and cell separation. *Anal Chem* 2007, 79:5117-5123.
8. Thévoz P. Adams J D, Shea H, Bruus H, Soh T: Acoustophoretic synchronization of mammalian cells in microchannels. *Anal Chem* 2010, 82: 3094-3098.
9. Dykes J, Lenshof A. Åstrand-Grundström I, Laurell T, Scheding S: Efficient removal of platelets from peripheral blood progenitor cell products using a novel micro-chip based acoustophoretic platform. *PLOS ONE* 2011, 6: e23074.
10. Cushing K W, Piyasena M E, Carroll N J, Maestas G C, López B A, Edwards B S, Graves S W, López GP: Elastomeric negative acoustic contrast particles for affinity capture assays. *Anal Chem*, in press.

11. Hu S, Ren X, Bachman M, Sims C E, Li G P. Albritton N: Surface modification of poly(dimethylsiloxane) microfluidic devices by ultraviolet polymer grafting. *Anal Chem* 2002, 74:4117-4123.
12. Fuard D. Tzvetkova-Chevolleau T, Decossas S, Tracqui P, Schiavone P: Optimization of poly-di-methyl-siloxane (PDMS) substrates for studying cellular adhesion and motility. *Microelectron Eng* 2008, 85:1289-1293.
13. Hellmich W, Regtmeier J, Duong T T, Ros R, Anselmetti D, Ros A: Poly(oxyethylene) based surface coatings for poly(dimethylsiloxane) microchannels. *Langmuir* 2005, 21: 7551-7557.
14. Efimenko K, Crowe J A, Manias E, Schwark D W, Fischer D A, Genzer, J: Rapid formation of soft hydrophilic silicone elastomer surfaces. *Polymer* 2005, 46:9329-9341.
15. Ferguson G S, Chaudhury M K, Biebuyck H, Whitesides G M: Monolayers on disordered substrates: self-Assembly of alkyitrichlorosilanes on surface-modified polyethylene and poly(dimethylsiloxane). *Macromol* 1993, 26: 5870-5875.
16. Linder V, Verpoorte E, Thorman W, de Rooij N F, Sigrist H: Surface biopassivation of replicated poly(dimethylsiloxane) microfluidic channels and application to heterogeneous immunoreaction with on-ship fluorescence detection. *Anal Chem* 2001, 73:4181-4189.
17. Owen M J, Smith P J: Plasma treatment of polydimethylsiloxane. *J Adhes Sci Technol* 1994, 8: 1063-1075.
18. Hermansan G T, From bioconjugate techniques. $2^{nd}$ edition. Oxford, UK: Elsevier: 2008: 940-945.
19. Stöber, W. & Fink, A. (1969). Controlled growth of monodisperse silica spheres in the micron size range. *Journal of Colloid and Interface Science,* 26: 62-69.
20. Xia, Y., Gates, B., Yin, Y., & Lu, Y. (2000). Monodisperse colloidal spheres: old materials with new applications. *Advanced Materials.* 12(10): 693-713.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A method for synthesizing elastomeric negative contrast acoustic particles having a functional vinyl group available for covalent modification, the method comprising:
    emulsifying an elastomer pre-polymer comprising the functional vinyl group with a catalyst in the presence of a surfactant under conditions sufficient to produce emulsion droplets;
    curing the emulsion droplets under conditions sufficient to form stable elastomeric negative acoustic contrast particles that have the functional vinyl group available for covalent modification; and
    contacting the negative acoustic contrast particles with biotin-PEG-tetrafluorophenyl azide under conditions sufficient to covalently modify the available vinyl functional group with biotin for binding to a target of interest.

2. The method of claim 1, wherein the elastomer pre-polymer comprises a silicone material.

3. The method of claim 1, wherein the elastomer pre-polymer comprises polyvinylmethylsiloxane (PVMS).

4. The method of claim 1, wherein the surfactant is a nonionic triblock copolymer surfactant.

5. The method of claim 4, wherein the nonionic triblock copolymer surfactant has greater than 50 end groups of polyethylene oxide (PEO).

6. The method of claim 5, wherein the nonionic triblock copolymer surfactant has a hydrophile-lipophile (HLB) value greater than 24.

7. The method of claim 1, wherein the target of interest comprises one of a cell, a protein, a receptor, an antibody, an antigen, a drug, virus, nucleic acid, a polysaccharide or a metabolite.

\* \* \* \* \*